US008229675B2

(12) United States Patent
Csore et al.

(10) Patent No.: US 8,229,675 B2
(45) Date of Patent: Jul. 24, 2012

(54) PATIENT INFORMATION BAR AND METHOD FOR TRACKING AND DISPLAYING BLOOD PRODUCTS

(75) Inventors: Miklos Csore, Sacramento, CA (US); Gerald F. Willman, Jr., Powder Springs, GA (US); Noah L. Bentley, Folsom, CA (US)

(73) Assignee: Global Med Technologies, Inc., Lakewood, CO (US)

( * ) Notice: Subject to any disclaimer, the term of this patent is extended or adjusted under 35 U.S.C. 154(b) by 1197 days.

(21) Appl. No.: 11/973,678

(22) Filed: Oct. 10, 2007

(65) Prior Publication Data

US 2008/0098329 A1    Apr. 24, 2008

Related U.S. Application Data

(63) Continuation-in-part of application No. 09/823,814, filed on Mar. 30, 2001, now Pat. No. 7,363,167.

(51) Int. Cl.
*G06F 19/00* (2011.01)
*G06Q 50/00* (2012.01)

(52) U.S. Cl. .............................................. 702/19; 705/2
(58) Field of Classification Search ........................ None
See application file for complete search history.

(56) References Cited

U.S. PATENT DOCUMENTS

| 5,505,685 | A | * | 4/1996 | Antwiler | 494/37 |
| 5,991,728 | A | * | 11/1999 | DeBusk et al. | 705/2 |
| 7,072,769 | B2 | * | 7/2006 | Fletcher-Haynes et al. | 702/21 |

FOREIGN PATENT DOCUMENTS

WO    WO 97/41525    * 11/1997

OTHER PUBLICATIONS

Triulzi (Transfusion Medicine (1995) vol. 9, No. 2, pp. 123-130).*
Brodheim, (Symposium on Computers in the Clinical Laboratory), "Automated Systems in Blood Banking," Clinics in Laboratory Medicine 1983, 3 (1): 111-132.
Butch, et al., "Electronic Verification of Donor-Recipient Compatibility: The Computer Crossmatch," Transfusion 1994; 34 (2): 105-109.
Cheng, "Experiences with 'Self Service' Electronic Blood Banking," Vox Sanguinis 1998; 74 (Suppl. 2): 427-429.
Cox, et al., "Remote Electronic Blood Release System," Transfusion 1997; 37(9): 960-964.
Safwenberg, et al., "Computerized Delivery Control—A Useful and Safe Complement to the Type and Screen Compatibility Testing," Vox Sanguinis 1997; 72: 162-168.

* cited by examiner

*Primary Examiner* — Lori A Clow
(74) *Attorney, Agent, or Firm* — The Reilly Intellectaul Property Law Firm, P.C.; Ellen Reilly; John E. Reilly

(57) ABSTRACT

A method and system for managing blood products and tracking their movement in which a database is provided for entering and storing information pertaining to each patient, and a patient toolbar is provided for selectively displaying patient information and condition including but not limited to each patient's special needs, prior transfusion reaction history, directed blood components, and blood type with a manual control button to selectively display each item or category of information on a screen.

27 Claims, 24 Drawing Sheets

PATIENT INFORMATION BAR AND METHOD FOR TRACKING AND DISPLAYING BLOOD PRODUCTS

CROSS REFERENCE TO RELATED APPLICATIONS

The present application is a continuation-in-part of patent application Ser. No. 09/823,814, filed 30 Mar. 2001, for METHOD AND SYSTEM FOR MANAGING BLOOD PRODUCTS, and incorporated by reference herein.

REFERENCE TO APPENDED ITEMS

Reference is made to SafeTrace Tx Table Administration Manual, Release v1.2.0.0 published November, 1999, SafeTrace Tx User's Guide, published November, 1999, and SafeTrace Tx Reference Manual, also published November, 1999, all published by Wyndgate Technologies of El Dorado Hills, Calif., said publications incorporated by reference herein.

BACKGROUND

This method and system relate to blood product management and more particularly relates to a novel and improved computerised method and system for blood product management including cross-matching and compatibility testing of blood products as well as the ability to display information about a patient during the preparation of blood components prior to transfusion and which is specifically adaptable for use in hospitals, clinics and the like.

There is a long-felt need for a blood product management system to help prevent the release of unsafe, unsuitable or ineffective blood products to patients. In a hospital, when an order comes down from a given floor or section of the hospital requesting blood, it is communicated to the blood bank which is typically located at the hospital. The blood bank will search for a suitable product for the patient, i.e. a suitable red blood cell, and in many situations must cross-match the blood product requested with the blood of the patient. Once successfully cross-matched, the blood product is then selected and made ready for issue. Another order or request will then be transmitted when the blood product is actually needed at which time the cross-matched product is delivered to the responsible personnel for providing a blood transfusion for the patient.

It is important to control the compatibility of a blood component and patient's blood to ensure safe transfusion of the component to the patient. This requires tracking of the patient blood attributes and blood component attributes by their respective antigens and antibodies. In addition, it is desirable to incorporate a patient information toolbar into the computer program for displaying and controlling critical patient information during the preparation of blood products prior to transfusion. This information includes patient special needs, patient comments, patient transfusion reactions, availability of autologous blood components, availability of directed blood components, significant antibodies, patient blood type, expiration of the current patient specimen, and reserved blood components.

The following definitions are given to assist in better understanding the system and steps followed in carrying out the present method and system:

"Antigen": A substance that induces the formation of antibodies and assists the body to distinguish between itself and a foreign substance.

"Antibody": A protein produced by the immune system in response to the presence of an antigen.

"Blood Type Definitions": A blood type is a way to classify blood into various groups. A blood type is determined by the presence or absence of antigens on the red blood cells, and the presence of antibodies in the serum. A blood type definition in the computer database is the combination of antibodies and antigens for each blood group (ABO/Rh).

"Blood Component": A blood component, also referred to as "blood product", is one of the portions of a unit of whole blood. Whole blood contains red blood cells, white blood cells and platelets suspended in a watery fluid called plasma. Blood components include red blood cells, plasma, platelets and cryoprecipitated antihemophilic factor (AHF).

"Significant Antibodies": Any antibody, other than those for A and B (which are expected), that might cause a serious ("hemolytic") reaction after transfusion of blood containing the corresponding antigen.

"Segment": A portion of the blood component that can be detached and subsequently used for testing.

"Product ID Tag": The Product ID Tag is attached to the blood product being processed or issued to a patient. It contains information about the patient and the blood product to help in the identification and validation of the patient and product. The Product ID Tag is one of the mechanisms that transfusion services and hospitals use to verify that the patient and the product are correctly matched before transfusion. A typical Product ID Tag consists of three different sections:

1. Patient Information Section. This section contains critical patient information necessary to identify the patient. It is used to identify the patient in regard to the hospital, blood type and blood antibodies, as well as special needs associated with the patient.

2. Product Information Section. This section contains relevant product specific information regarding unit of blood to which this section is physically attached. This section is used to identify the unit of blood, blood type, and antigens. In addition to the product information, it contains information regarding cross-match testing, and lists any prohibiting factors and comments relevant to issuing of this product to the patient identified in the Patient Section of the report.

3. Transfusion Information Section. This section is created for recording handwritten information during transfusion. This section is a form that is filled out by the technician before, during and after transfusion of the product attached to the report. This section is used to record relevant information to the transfusion process, which can later be entered into the computer program database.

Accordingly, there are specific requisites to reliable, secure cross-matching of certain blood products, namely, receiving an order for the blood product, tracking segments of the blood components in inventory, locating a specimen of the patient's blood and transferring it to a given location, which typically would be a lab or blood bank at the hospital where the inventoried blood segments are located.

It is therefore desirable to control the remote testing of compatibility of a blood product and patient specimen to ensure the safety of the blood component transfusion into the human body by using a segment of the blood product assigned at the lab and mixing it with a portion of the patient specimen so as to achieve efficiency in the delivery of blood components both for emergency and non-emergency situations.

Another aspect is to provide a computerised system that enables remote testing of patient blood and a segment of the blood component intended for transfusion remotely through the steps of (a) assigning a blood product, which is typically stored at a central facility, to a patient for testing at the central facility and preparing a segment of the blood component; (b) transferring to the facility a blood specimen drawn from the patient; (c) testing the segment of the blood component assigned with the blood specimen drawn from the patient to determine their compatibility; (d) whether or not compatible, printing a product ID tag at the facility where the blood component is located; and (e) continuously tracking movement of the blood product and specimen between the central facility and hospital on a database.

Another aspect is to track patient blood attributes and blood component attributes in such a way as to ensure that the attributes are compatible with each other as well as to ensure that the transfused blood component is compatible with the patient who is receiving the transfusion.

A further aspect is to provide for a novel and improved patient toolbar having a row of icons for displaying critical patient information during the preparation of blood products prior to transfusion so as to make readily available to the medical technician important current and historical information about the patient.

Accordingly, a method of managing and tracking blood products is provided for use between a plurality of remote patient facilities and a central blood testing facility wherein a blood specimen is obtained from each patient who requires a blood reserve, selecting a blood product for cross-matching with each said patient specimen, cross-matching each said patient specimen and said blood product to determine their compatibility with one another, and providing a database for the entry of information pertaining to each patient and a toolbar for displaying same. The step of storing and selectively displaying information is further characterized by the ability to quickly display the presence or absence of information via a row or series of button icons relating to a patient's special needs, prior transfusion history, autologous blood availability and its location, blood type and patient specimen expiration date; and still further, the ability to quickly display information relating to the location of patient blood attributes in the database.

A system has been devised for managing and tracking blood products between a central blood test facility and a plurality of remote facilities which includes means for recording information on a database which identifies each patient requiring a blood reserve, a toolbar having an icon for obtaining a blood specimen from each said patient, an icon for assigning a segment of a blood product for cross-matching and for cross-matching each said segment and patient specimen to determine their compatibility with one another, and an icon for identifying each segment and patient specimen determined to be compatible as well as storing same in the computer.

The foregoing examples and objects are intended to be illustrative and not exclusive. Other limitations of the related art will become apparent upon a reading of the Specification and study of the Drawings. In addition to the exemplary aspects and embodiments described above, further aspects and embodiments will become apparent by reference to the Drawings and by study of the following Description.

BRIEF DESCRIPTION OF THE DRAWINGS

FIG. 20 is a screen display of patient information;

FIG. 22 is a screen display of information stored in tracking the location of blood components.

Exemplary embodiments are illustrated in referenced Figures of the drawings. It is intended by the embodiments and Figures disclosed herein, that these are to be considered illustrative rather than limiting.

DETAILED DESCRIPTION

The embodiment to be described allows a blood bank to maximize its efficiency in cross-matching a blood component to a patient for transfusion. This efficiency will result in improved patient care by the blood bank and the hospital. This process allows timesaving during the testing and the time needed to transfer the blood product to the patient site. The requirements for this process are to have complete tracking of the blood component, the blood component segment, the patient, and the patient specimen. Any one of these requirements not met could result in a mismatch of the component and the patient which can result in serious health problems to the recipient of the blood.

Figure 1:
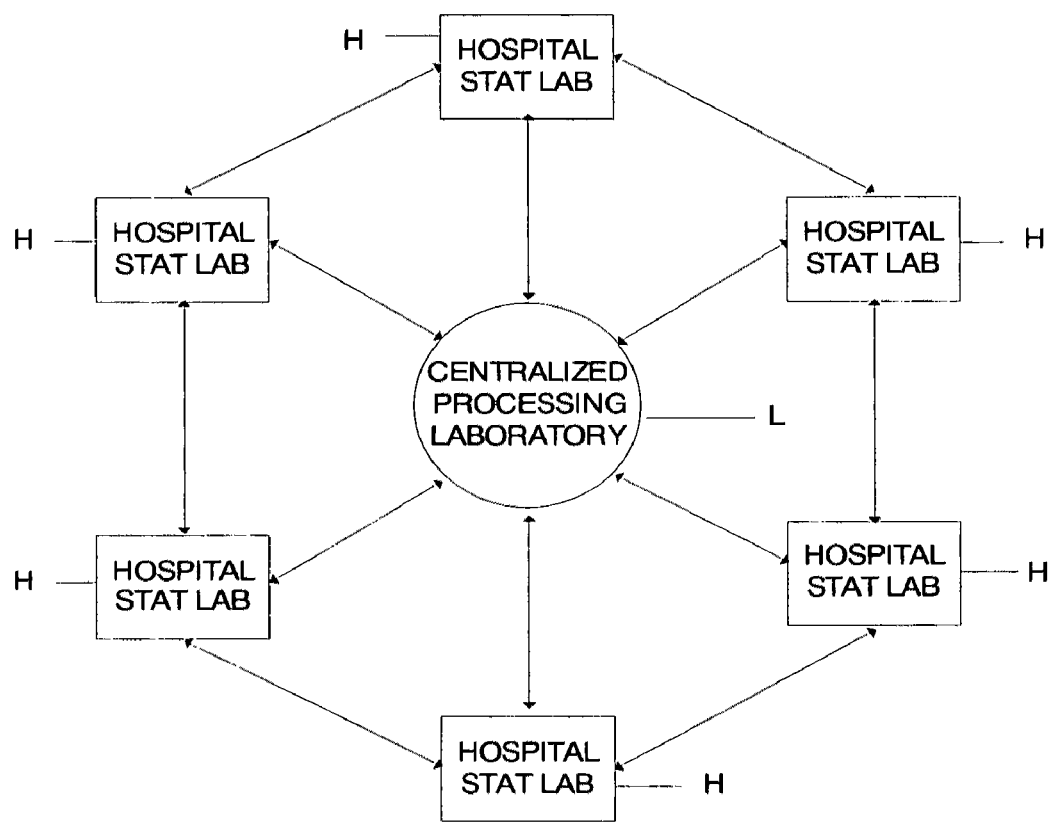
FIG. 1 is a flow diagram of a centralized transfusion model with multiple hospitals.

The remote cross-match capability allows a group of hospitals to be organized to include a common or centralized facility or transfusion service to share a common laboratory to perform blood testing as well as cross-match work for all hospitals in the group. This reduces the amount of staff required at the hospitals. Typically, each hospital will have only a stat laboratory to handle its emergency patient/product cross-match needs. FIG. 1 depicts a typical centralized or common transfusion model L having a "centralized processing laboratory l" with multiple hospitals H.

Accordingly, the hospital is able to track the location of the patient specimen, segment of the blood component and the blood component itself. The cross-match compatibility testing is completed using the segment of the blood component and the patient specimen while the blood component resides at a different location. This process will allow efficient and timely delivery of blood components in both emergency and non-emergency situations.

Figure 2:
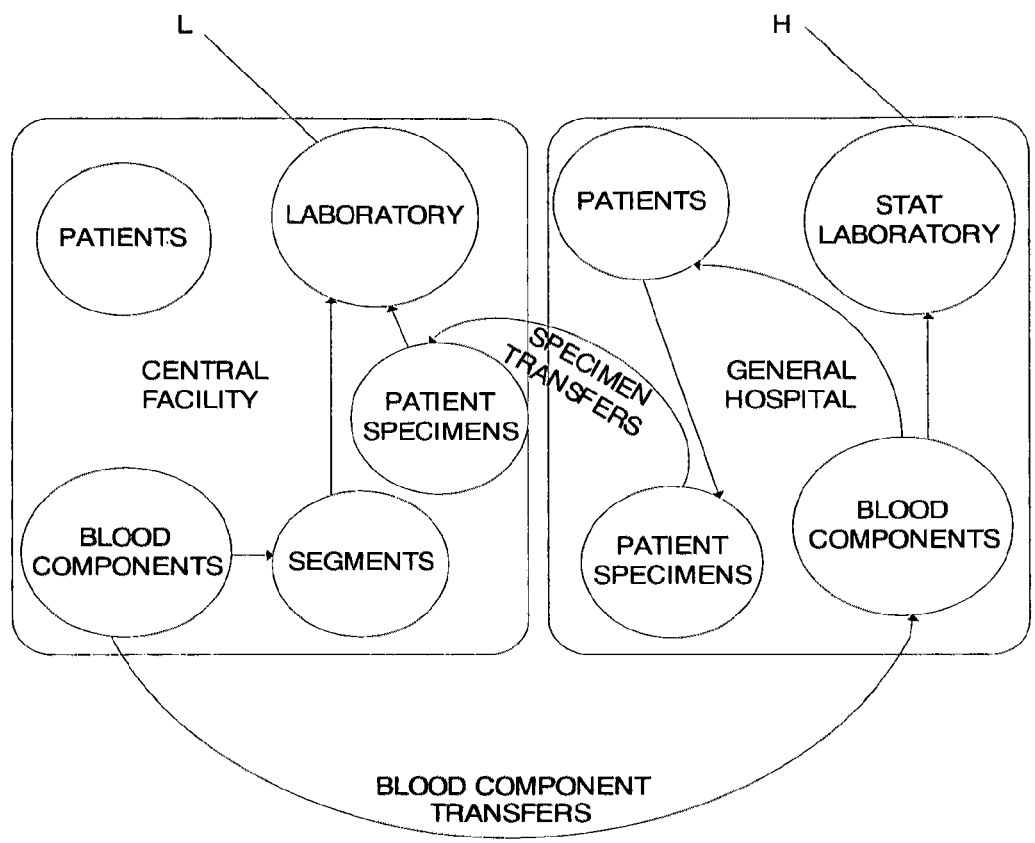
FIG. 2 is a flow diagram of a central facility and one of the hospitals illustrated in FIG. 1 which illustrates the location of inventory, segments, patient specimens and patients.

Before a remote cross-match can be performed, the following conditions must exist: (a) the patient exists in the system with current visit information, (b) the patient has a current blood specimen and the specimen has been transferred to the central facility, (c) the patient has an order for a blood component and a cross-match test, (d) the blood component has an available segment, and (e) the blood component that will fill the order resides at the hospital where the patient is located and a segment of that blood component is at the central facility with laboratory L. FIG. 2 depicts a central facility including the laboratory L and one of the hospitals H and where the inventory, segments, patient specimens and patients are located.

Completing the remote cross-match is the process wherein a lab technician at the central laboratory L assigns a blood component identified by a segment to a patient specimen. Once the assignment is made, the lab technician proceeds to test the segment with the patient specimen to determine compatibility. Upon completing the cross-match test, the lab technician enters the results into the computer program database. Once the results are saved, the product ID tag will be printed at the location of the blood component L and the blood component will be ready to issue to the patient if the patient and product are compatible.

Figure 3:
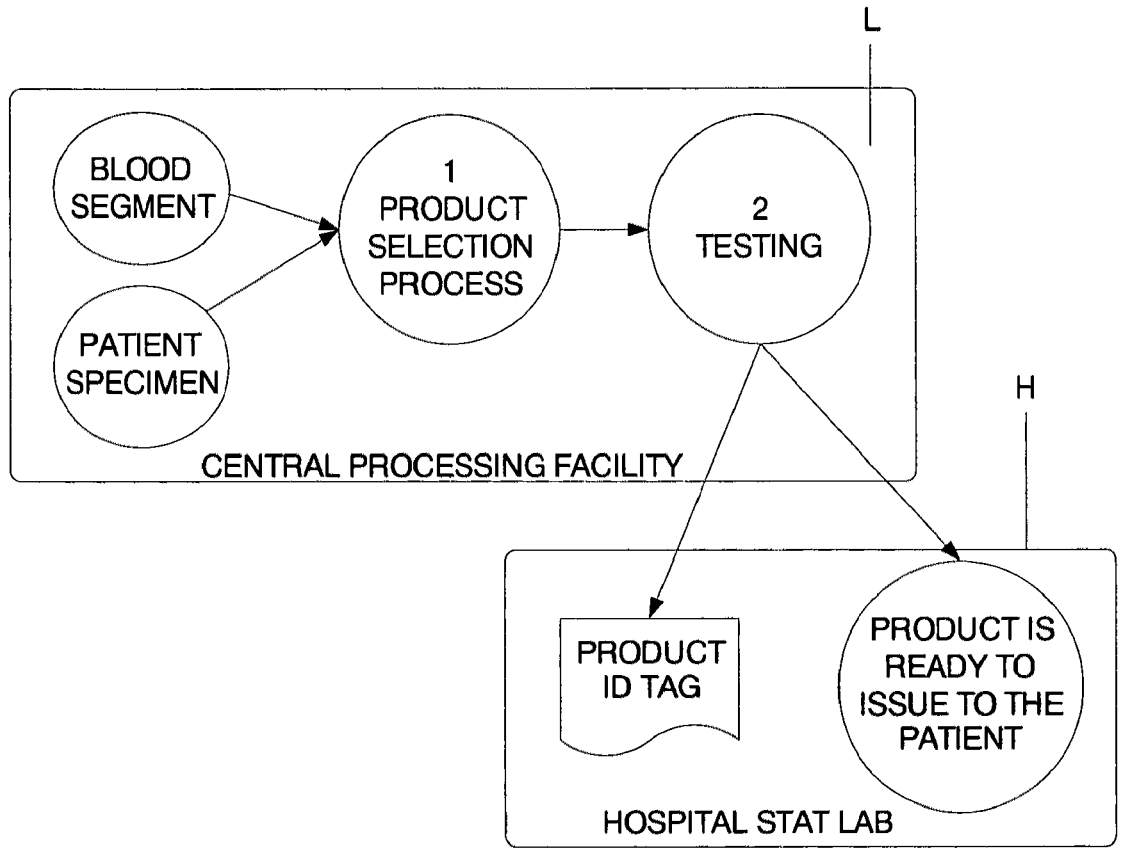
FIG. 3 is a flow diagram illustrating completion of remote cross-match testing.
Figure 18:
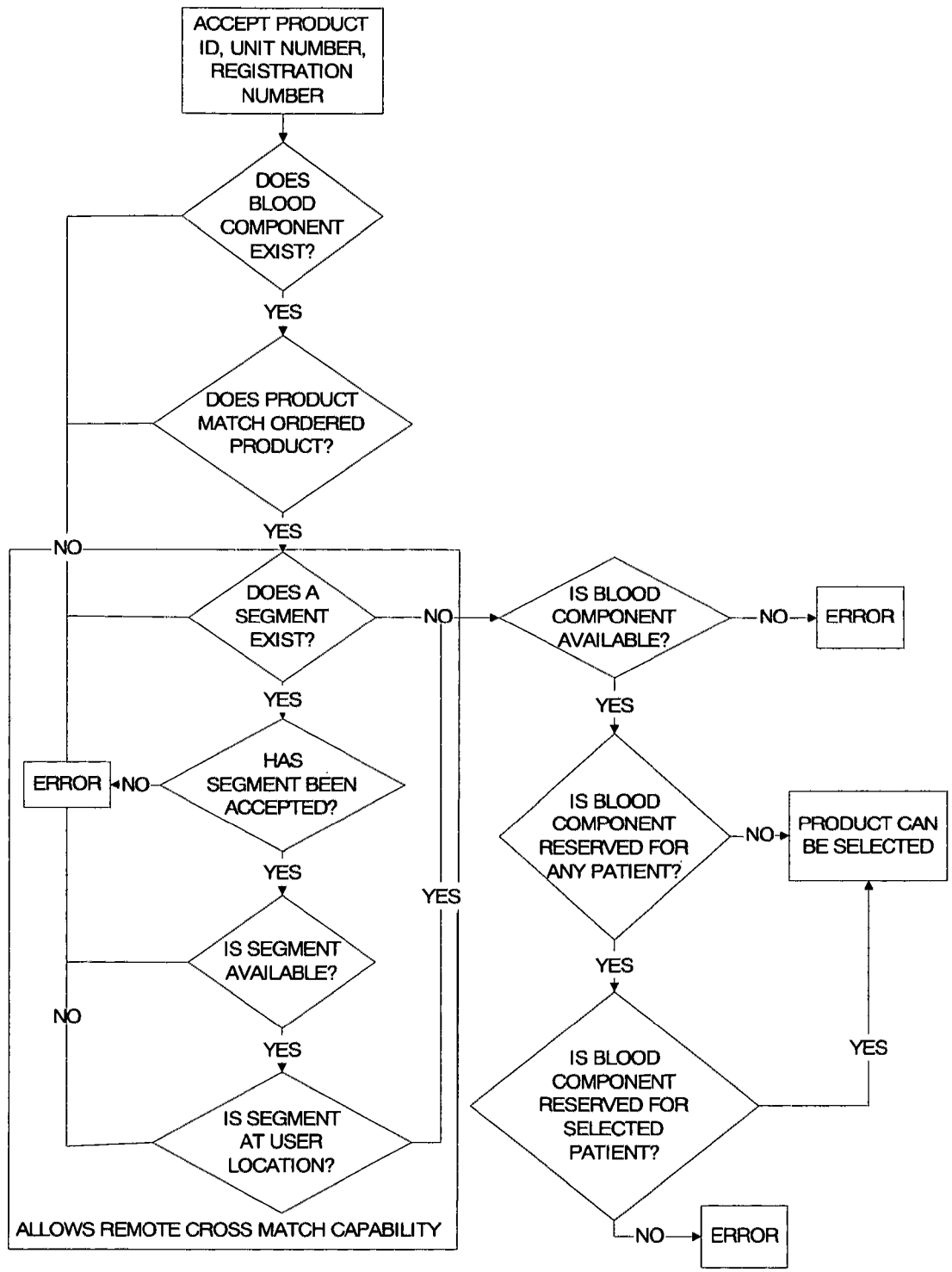
FIG. 18 is a flow chart showing product selection steps followed in remote cross-match testing.
Figure 19:
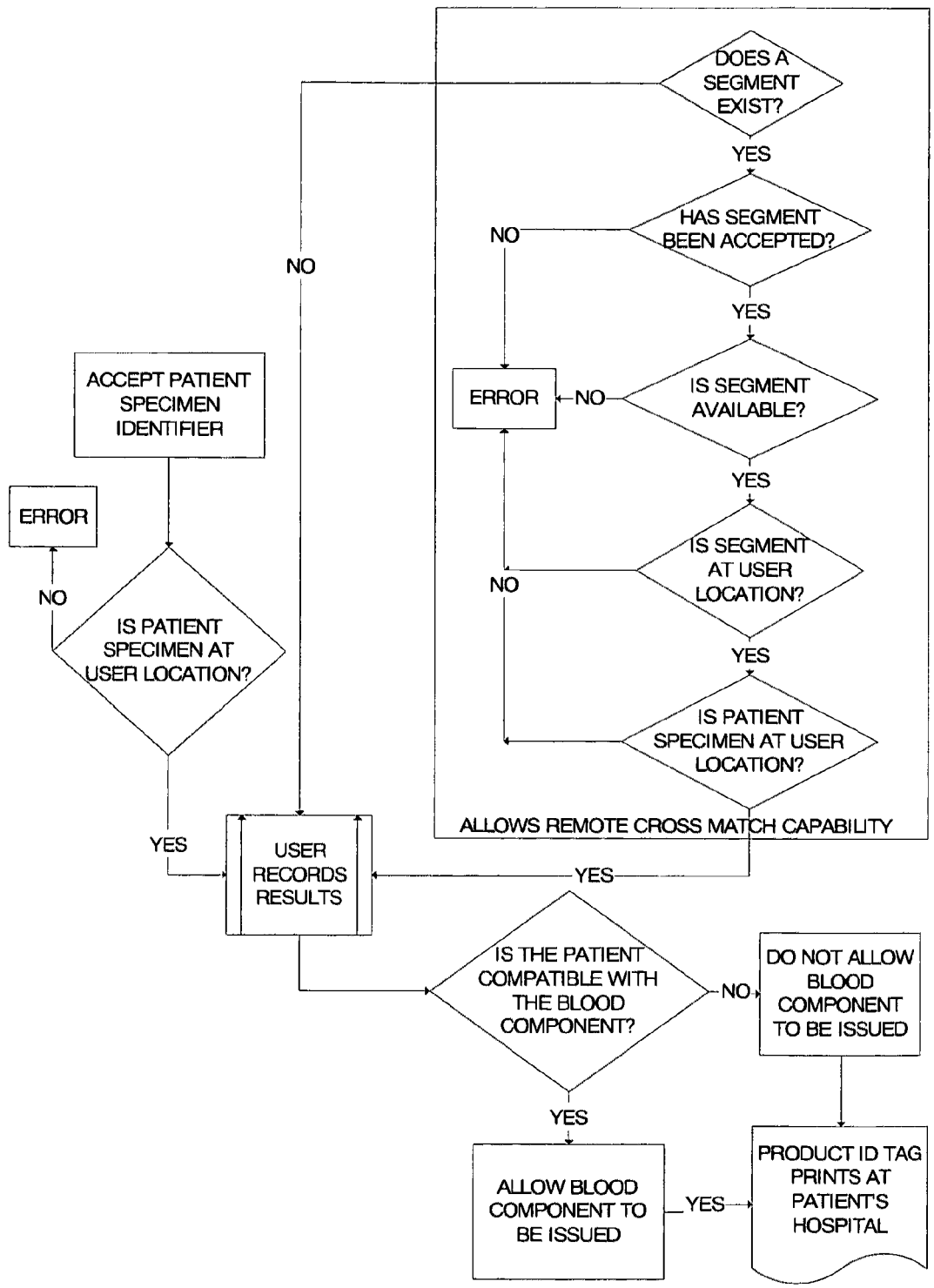
FIG. 19 is a flow chart illustrating test result entry steps related to remote cross-match functionality.

As shown in FIG. 3, the laboratory technician at the central facility assigns a blood component identified by the segment to the patient. During this product selection process, as shown in FIG. 18, the computer program runs the following checks: (a) verifies that the product ID of the entered component matches the selected order item; (b) if the entered component has an active segment, then the segment must be entered by clicking the segment command button; (c) verifies the location and status of the segment (the segment must be available and located at the facility making the selection); (d) verifies the state of the component; and (e) if the entered component is reserved, make sure that the component is reserved for the designated patient. In testing, the laboratory technician performs the cross-match test at the work bench. Upon completion of the serological testing, the technician enters the results into the computer program database. The computer program database forces the technician to verify the patient specimen identifier and the blood component segment identifier before allowing them to record the results of the test. During the result entry process, as shown in FIG. 19, the computer program runs the following checks: (a) verifies that the specimen is at the user's location for abbreviated or unabbreviated cross-match test and (b) verifies that the segments are at the user's location for abbreviated or unabbreviated cross-match test.

When the technician has completed the data entry of the test results, the results are written to the database. For each completed cross-match test, a product ID tag is printed at the facility where the blood component is located. Any blood components associated with cross-match tests that were compatible will be available for issue at the location of the patient and blood component.

Figure 4A:
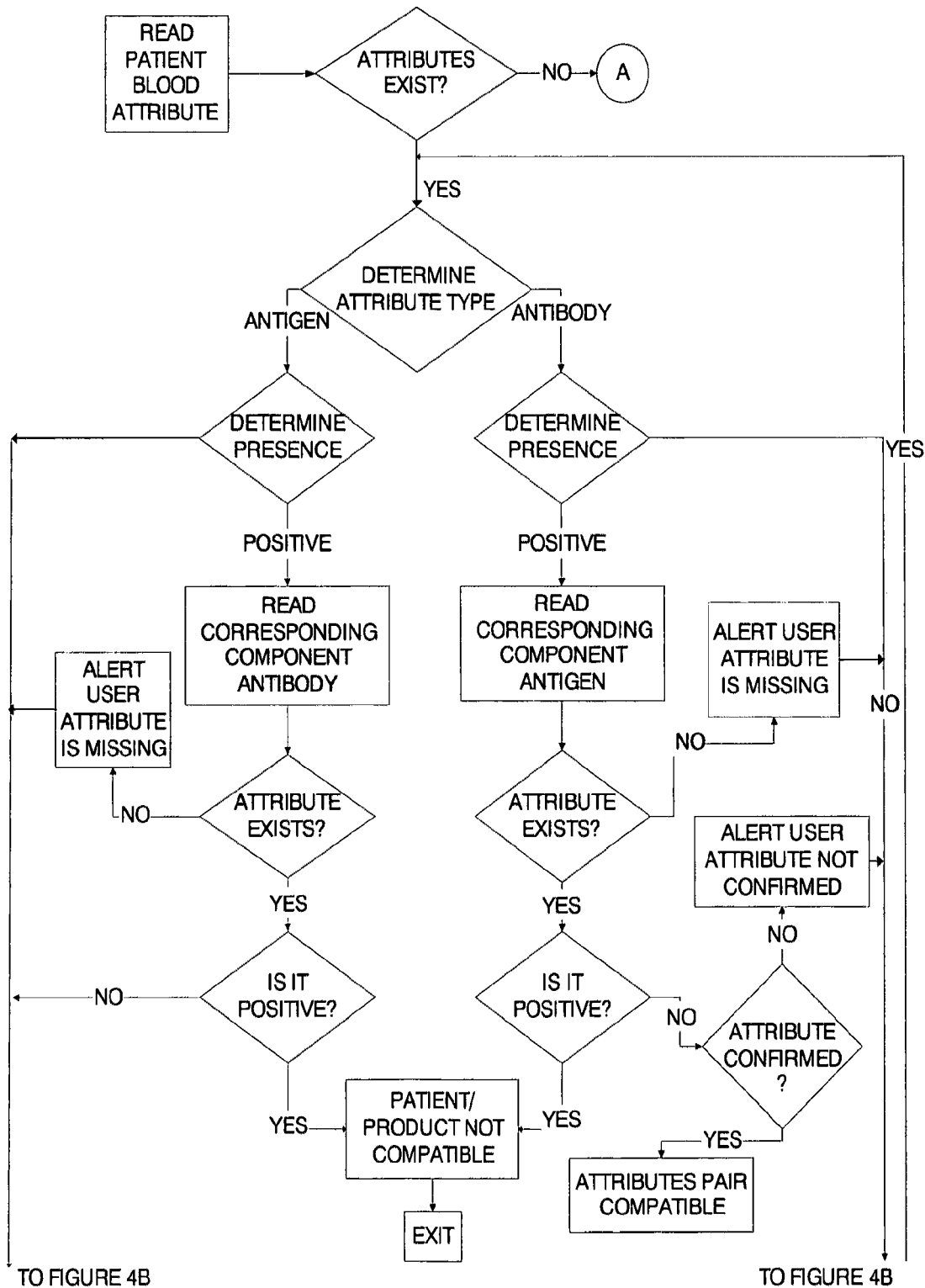
FIG. 4 is a flow chart illustrating the logic used in a standard compatibility test.
Figure 4B:
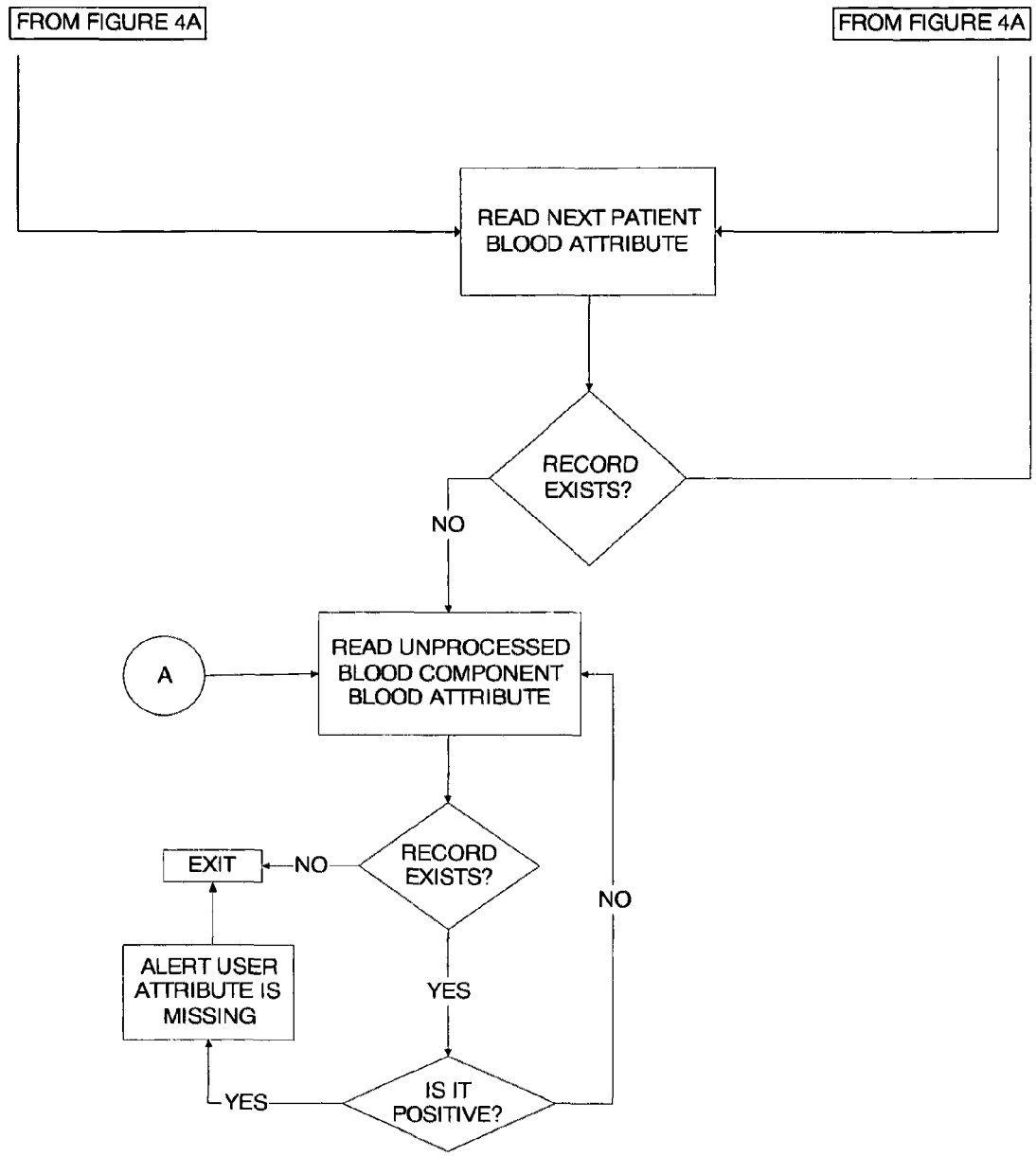

Patient/product compatibility is carried out by determining the patient blood attributes and the blood component attributes by their respective antigens and antibodies. As shown in FIG. 4, standard compatibility compares the patient's antigens with the blood component's corresponding antibodies and blood component's antigens with the patient's corresponding antibodies. When comparing the corresponding antigen and antibody pairs, the incompatibility is determined by a positive presence in both the antigen and antibody. Further, the blood component antigen or antibody may require confirmation by the blood bank for the compatibility comparison to be successful. As illustrated in FIG. 4, when this situation occurs, the user is alerted that a blood component's blood attribute has not been confirmed by the blood bank. If one-half of the pair is missing either from the patient or the blood component, the user is alerted that a blood attribute is missing; further testing on the patient's blood or the blood component is required to determine compatibility.

The following Table illustrates a sample compatibility test between the patient and the blood component:

TABLE I

| Patient Antibody | Component Antigen | Component Attribute Confirmed | Compatible |
| --- | --- | --- | --- |
| K Positive | K Positive | N/A | No |
| K Positive | K Negative | Yes | Yes |
| K Positive | K Negative | No | Unknown |
| K Positive | K Unknown | N/A | Unknown |

FIG. 4 illustrates the logic employed in carrying out standard compatibility tests.

Auto-compatibility compares the antigens and antibodies within either the patient or within the blood component. The new or updated antigen is compared with the corresponding antibody or the new or updated antibody is compared with the corresponding antigen. If both the antigen and antibody have a positive presence, then the patient or blood component is incompatible with itself. When this situation occurs, the computer program database alerts the user that the new or updated blood attribute is not compatible with the existing blood attribute information. These checks help reduce data entry errors.

Figure 5:
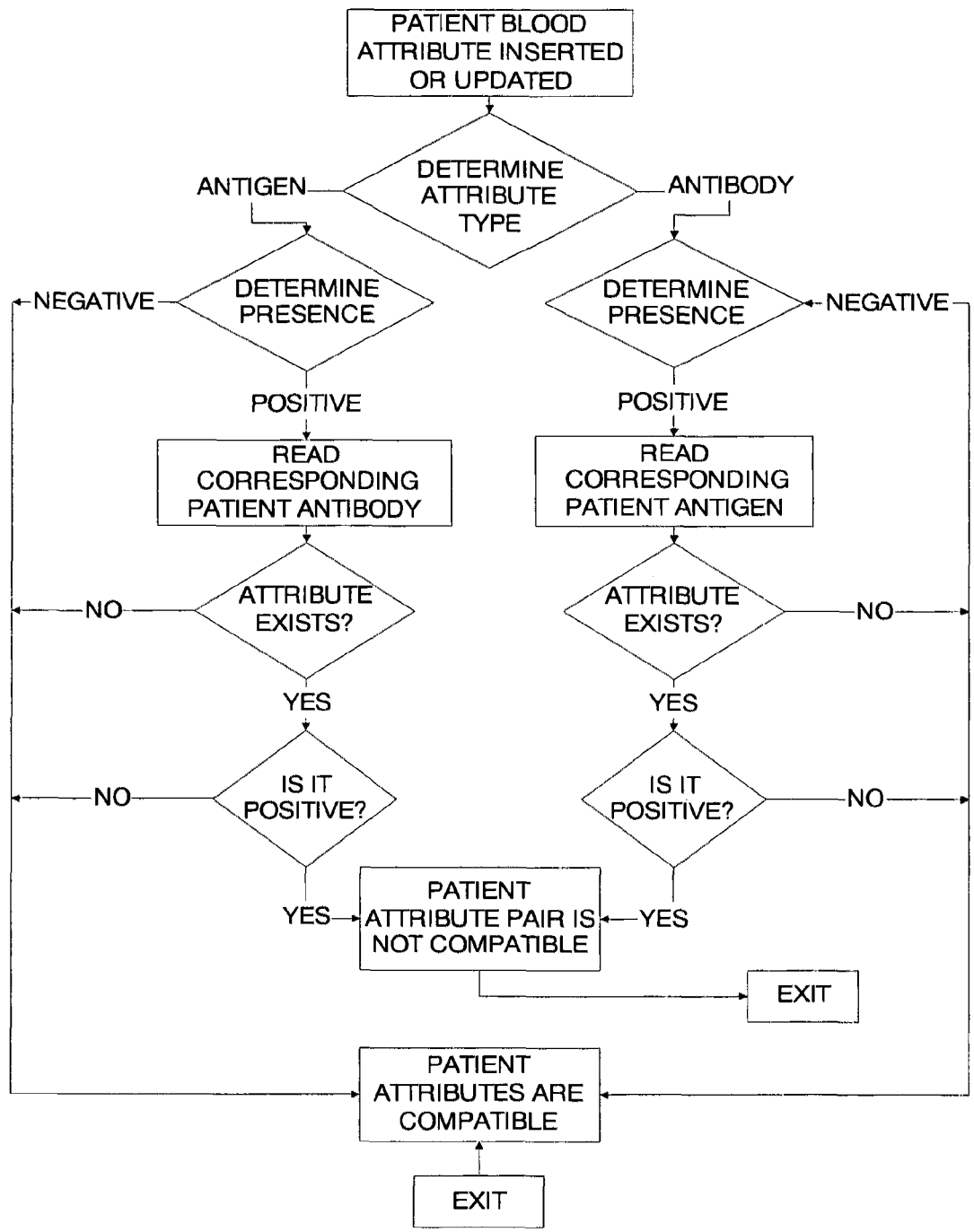
FIG. 5 is a flow chart illustrating the logic used in a patient auto-compatibility test.
Figure 6:
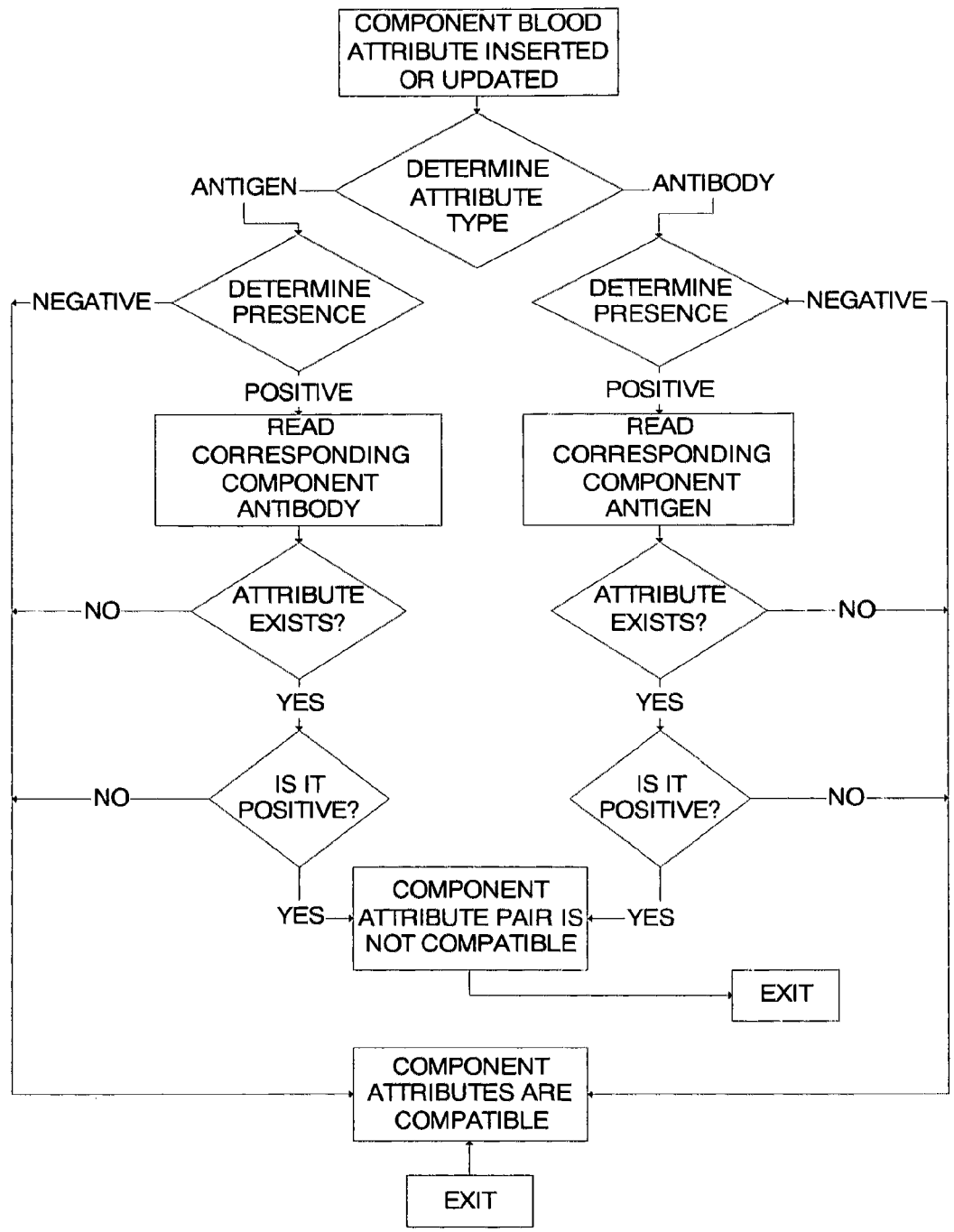
FIG. 6 is a flow chart illustrating the logic used in a product auto-compatibility test.

FIG. 5 illustrates the logic used in testing patient auto-compatibility, and FIG. 6 illustrates the logic used in testing blood component auto-compatibility.

Figure 7A:
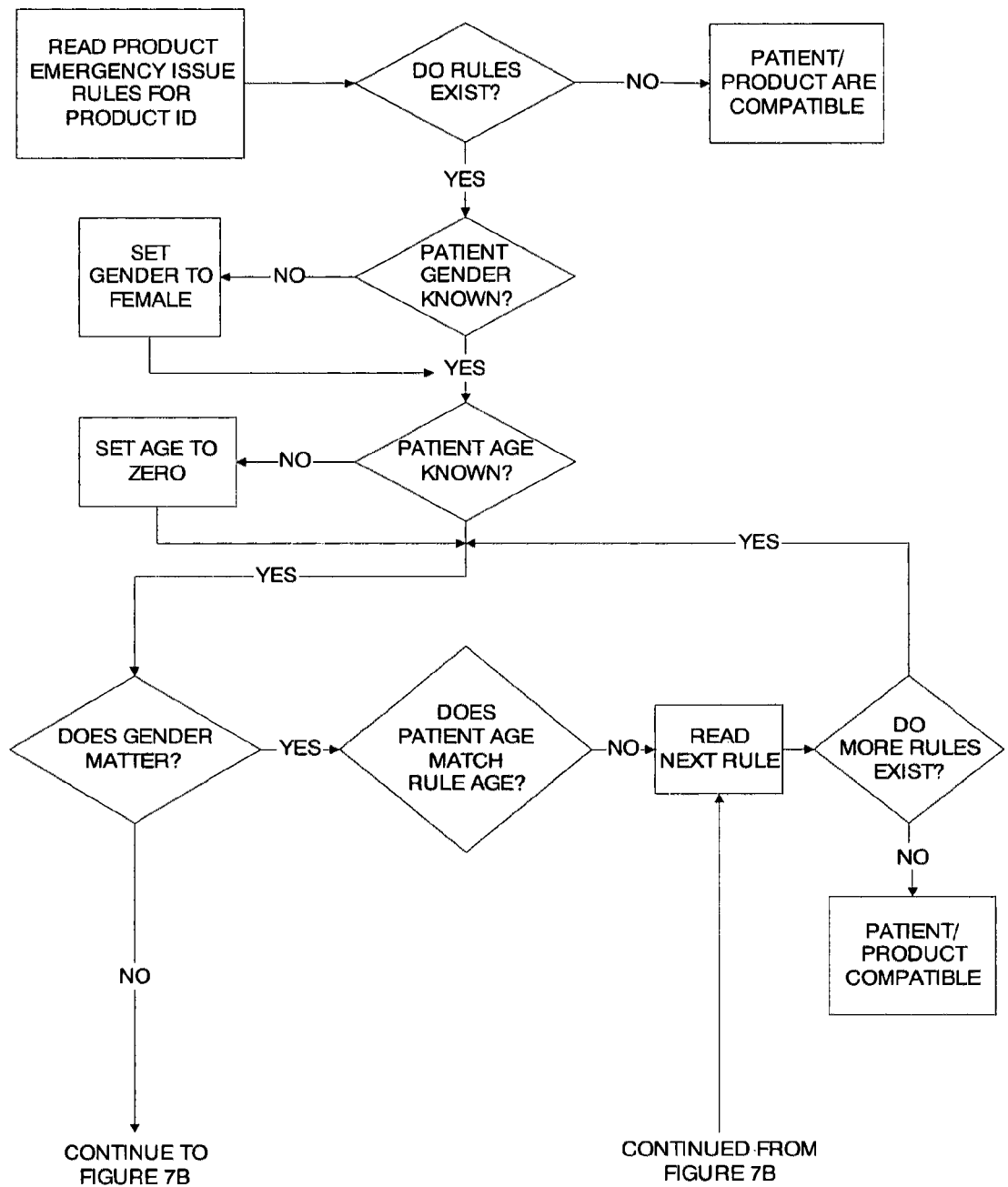
FIG. 7 is a flow chart illustrating the logic used in an emergency patient product compatibility test.
Figure 7B:
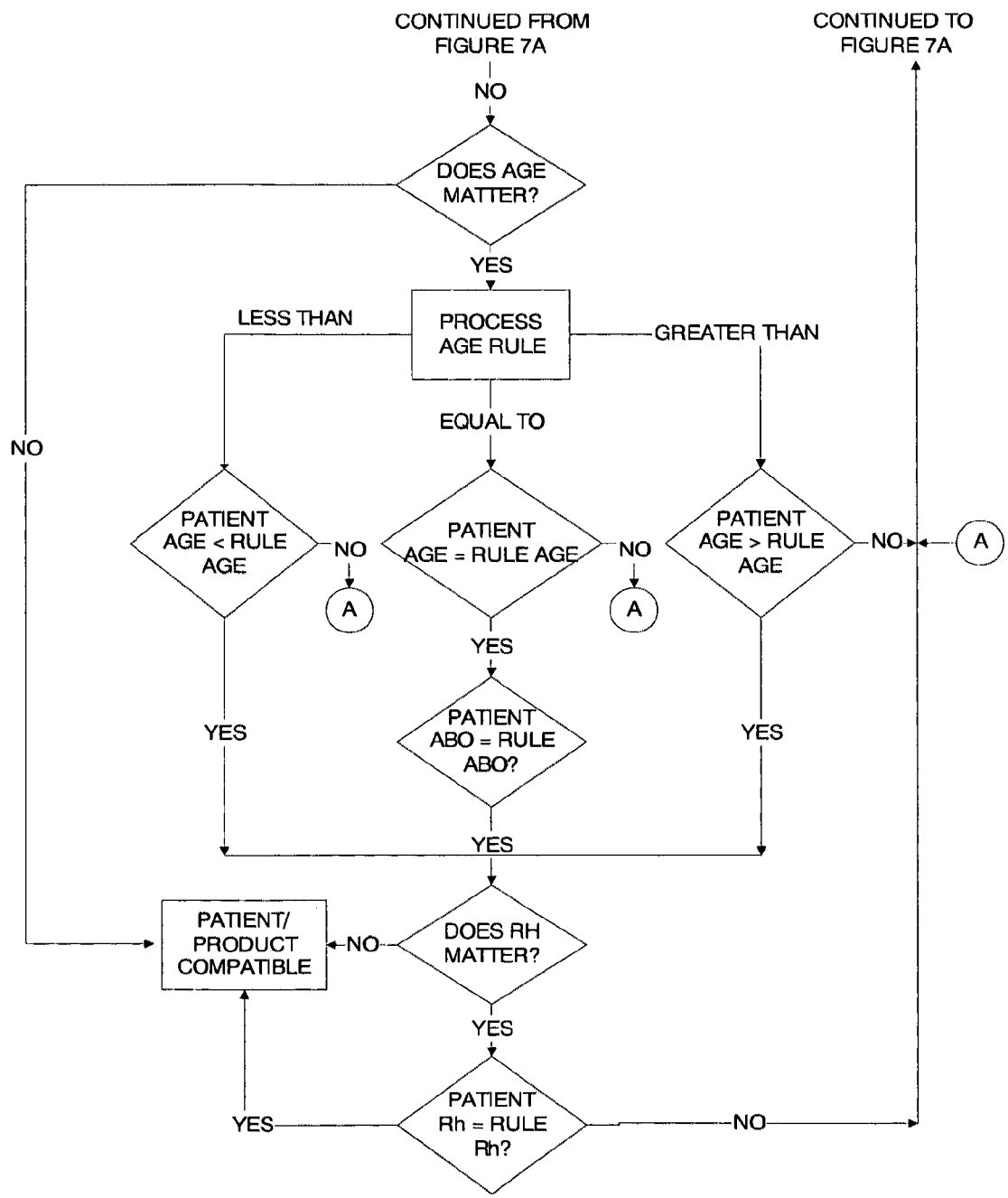

When the patient is unknown to the computer system or the patient is known but there is no current specimen and/or no blood type test on the current specimen, as illustrated in FIG. 7, an emergency compatibility check is run to determine if the blood component selected can be issued to the patient. The emergency issue results are controlled by the users to fit the industry defined standards for a given product ID. The following Table illustrates a sample of the rules that may be used by a blood bank:

TABLE II

| Product ID | Age Operator | Age | Gender | ABO | RH |
| --- | --- | --- | --- | --- | --- |
| RBC | Greater than | 50 | Female | 0 | |
| RBC | Less Than | 50 | Female | 0 | Neg |
| RBC | | | Male | 0 | |
| FFP | | | | AB | |
| Gran | Greater than | 50 | Female | 0 | |
| Gran | Less Than | 50 | Female | 0 | Neg |
| Gran | | | Male | 0 | |

Figure 8:
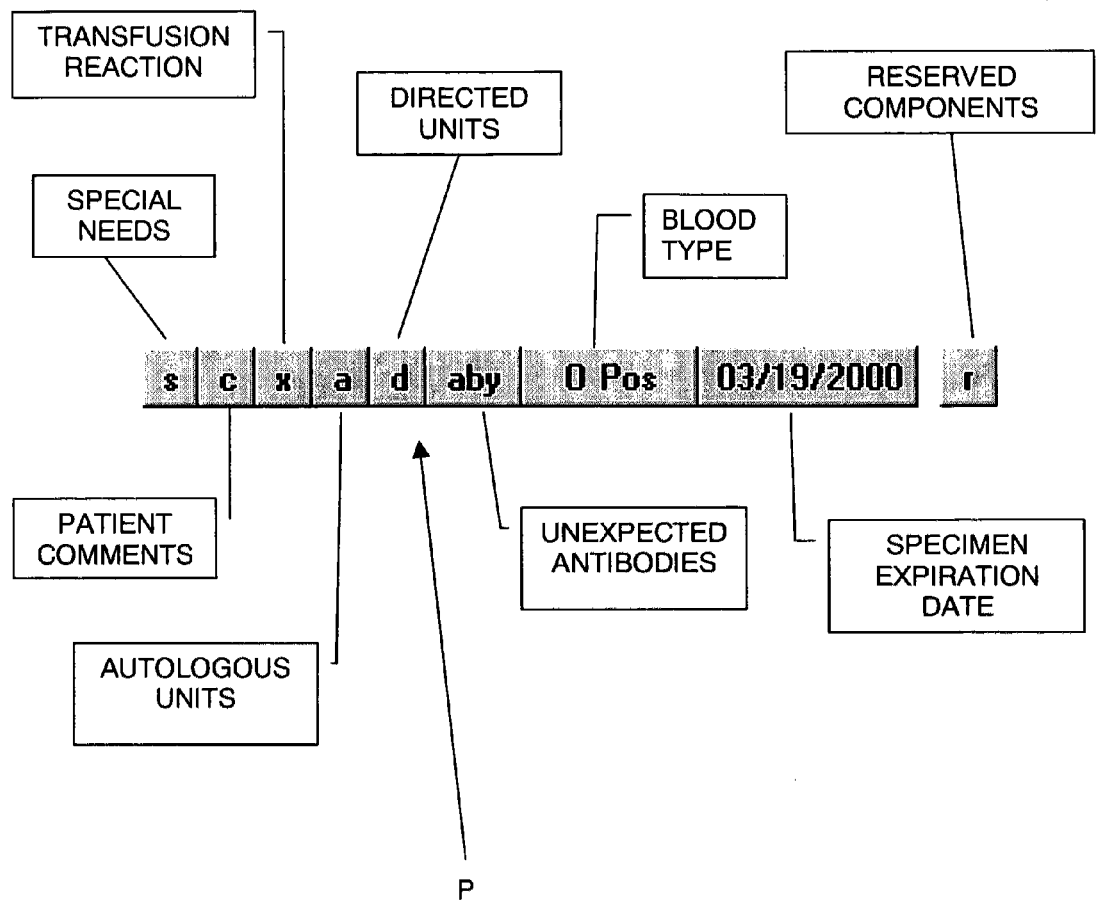
FIG. 8 is a screen display of a patient bar.
Figure 20:
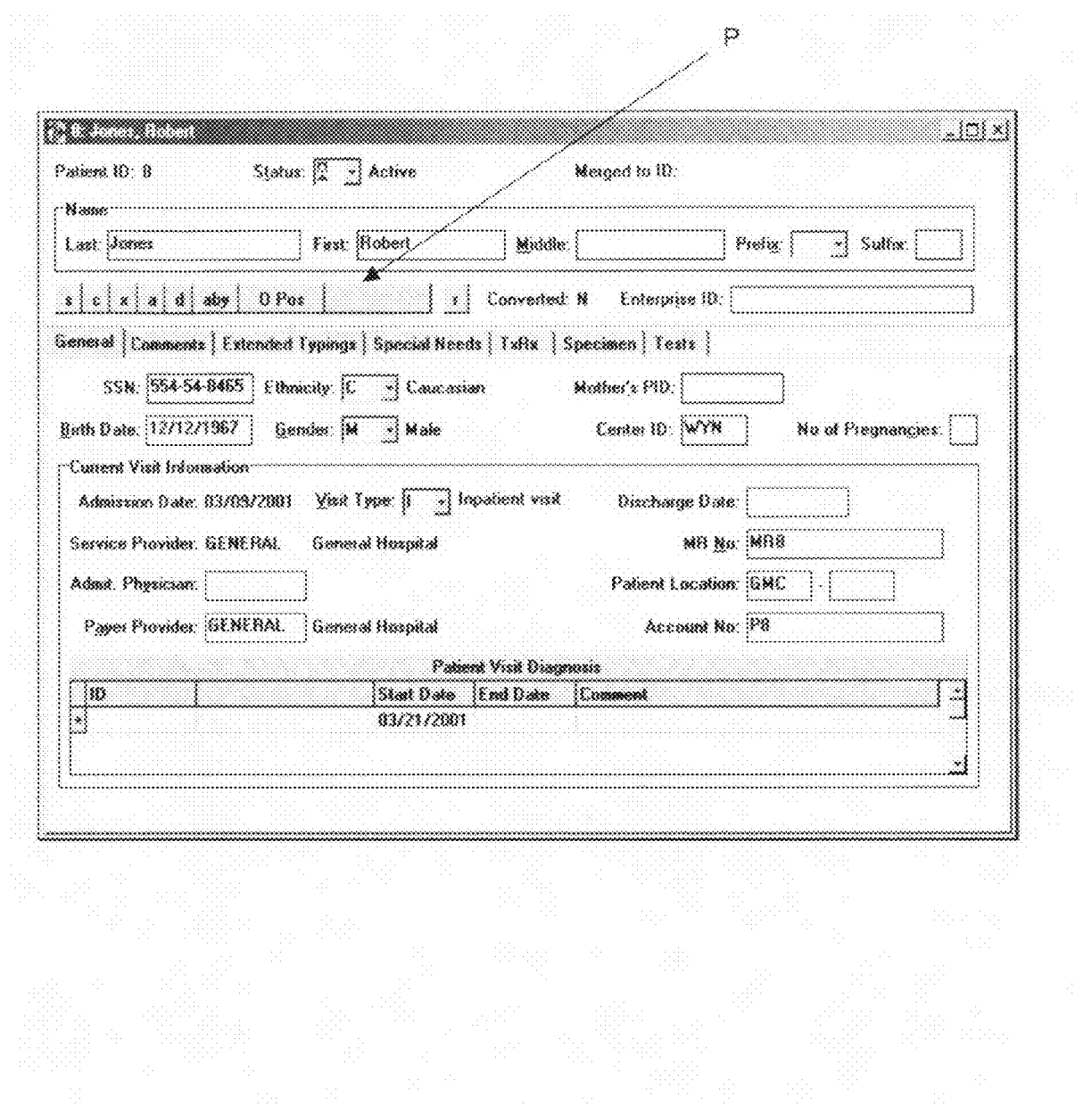

There is illustrated in FIG. 8 a patient bar P which affords access to information stored in the computer pertaining to each patient and blood products for that patient which is correlated with a patient identification number used to uniquely identify each patient in the database. FIG. 20 illustrates a typical patient profile screen which displays the patient bar P in conjunction with a particular patient having a patient identification number as displayed at "Patient ID".

Button captions are driven by the current state of patient information which is drawn from the database.

Specifically, the button s provides a visual indication that the patient has special needs. If the button displays as a capital "S", then there are active special needs for the patient; otherwise, a lower case "s" means no current special needs exist, as illustrated in FIG. 8. Clicking the button s accesses the patient's special needs information stored in the computer on a patient profile form. Patient special needs information is defined by the client and normally includes clinical information about the patient that constrains the scope of blood products which are appropriate for use by a particular patient. These needs are most often critical safety indicators which must be considered when selecting blood products for patient transfusion. Failure to consider patient special needs when selecting and testing blood products can be considered as a serious safety issue.

Figure 9:
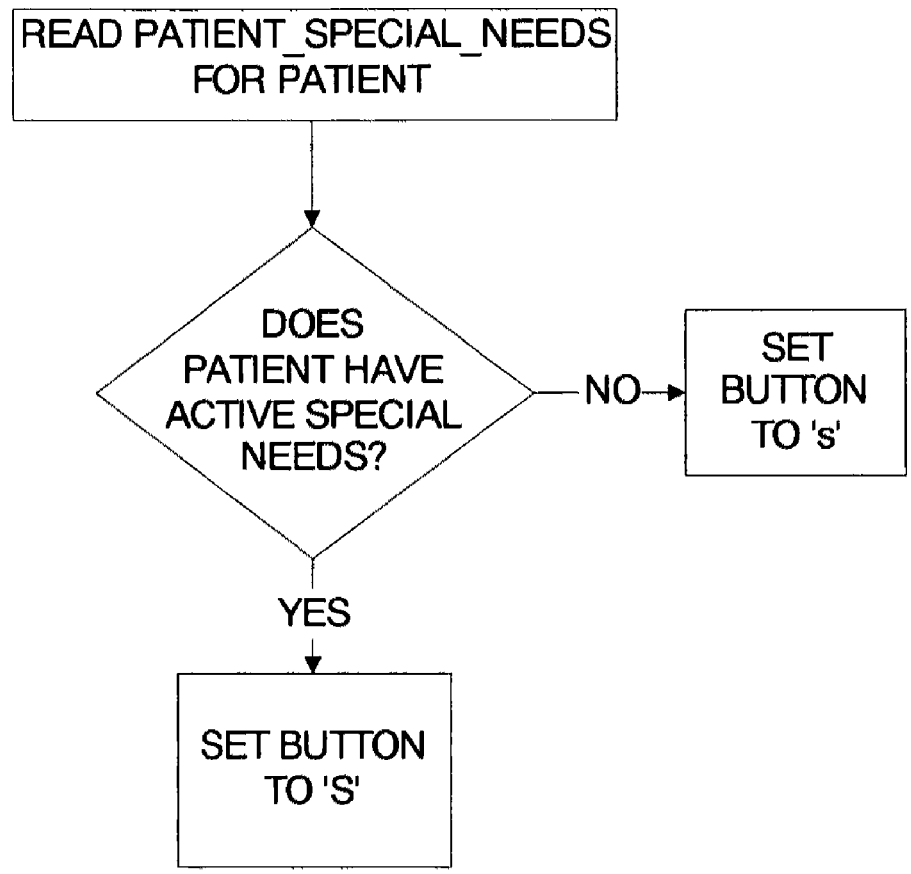
FIG. 9 is a flow chart illustrating the logic used in button s of the patient bar.

A patient "comments" button c provides a visual indication of patient comments. Again, if the button c displays as a capital "C", then there are active comments; otherwise, a lower case "c" means no current comments exist, as illustrated in FIG. 9. Clicking the button C accesses any patient comments as stored in the computer.

Patient transfusion reaction information is used to document clinical information about the patient when the patient has had a reaction to a prior transfusion. This type of reaction is often followed up by subsequent post-transfusion testing to help determine the possible causes of the reactions. A reaction history may constrain the scope of blood products which are appropriate for use by a particular patient. Failure to consider prior transfusion reaction information when selecting and testing blood products may be considered a serious issue.

Figure 10:
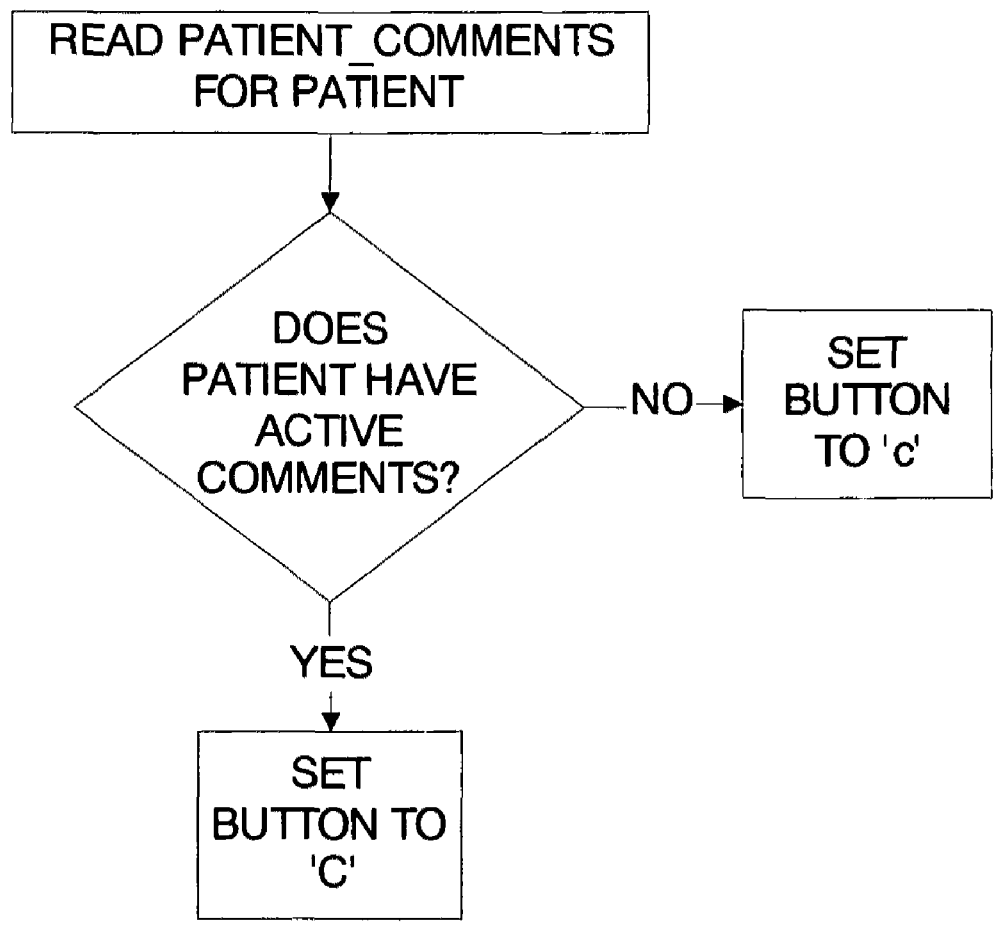
FIG. 10 is a flow chart illustrating the logic used in button c of the patient bar.

The button x provides a visual indication of transfusion reaction information of a patient. Thus, an upper case "X" indicates that the patient has had a transfusion reaction; otherwise, a lower case "x" means no transfusion reaction has been recorded in the system as illustrated in FIG. 10. Clicking the button X accesses any transfusion reaction information stored in the computer.

Figure 11:
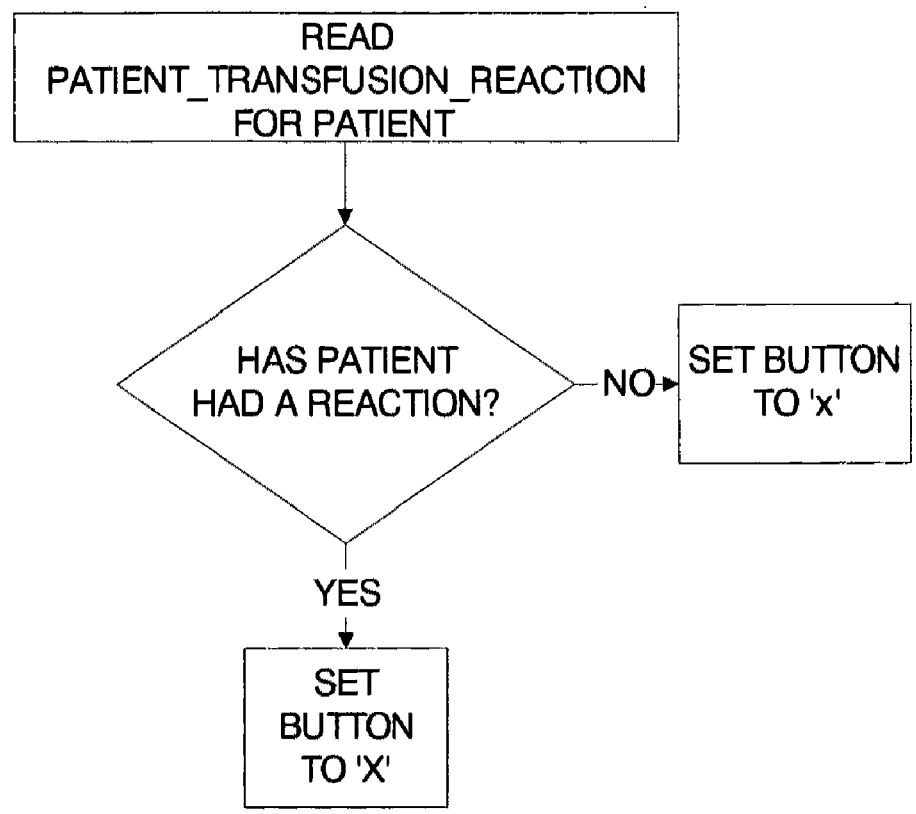
FIG. 11 is a flow chart of the logic used in connection with the button x of the patient bar.

The button a provides a visual indication of the availability of at least one unit that is identified as an autologous donation for the patient which has not expired, not transfused, not shipped, not discarded, not consumed or crossed-over. If the button displays a capital or uppercase "A", there is at least one such donation in inventory; otherwise, a lower case "a" means "none", as illustrated in FIG. 11.

Autologous components are blood products (i.e. whole blood) which the patient has donated specifically for his or her personal use. A patient who is scheduled for surgery where a transfusion may be required will often donate blood prior to surgery. This blood is categorized as autologous and is the preferred choice for transfusion.

Figure 12:
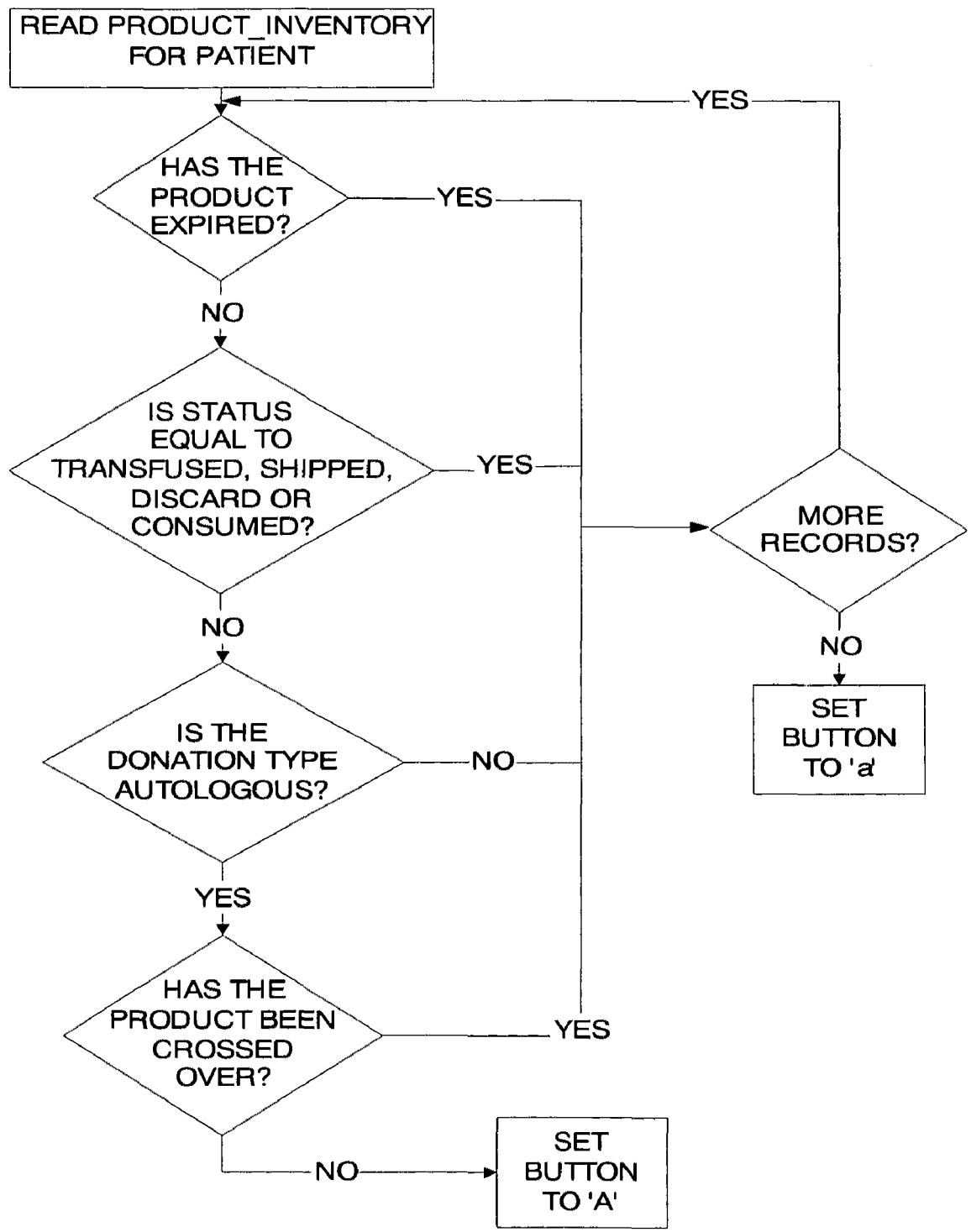
FIG. 12 is a flow chart of the logic used in button a of the patient bar.
Figure 13:
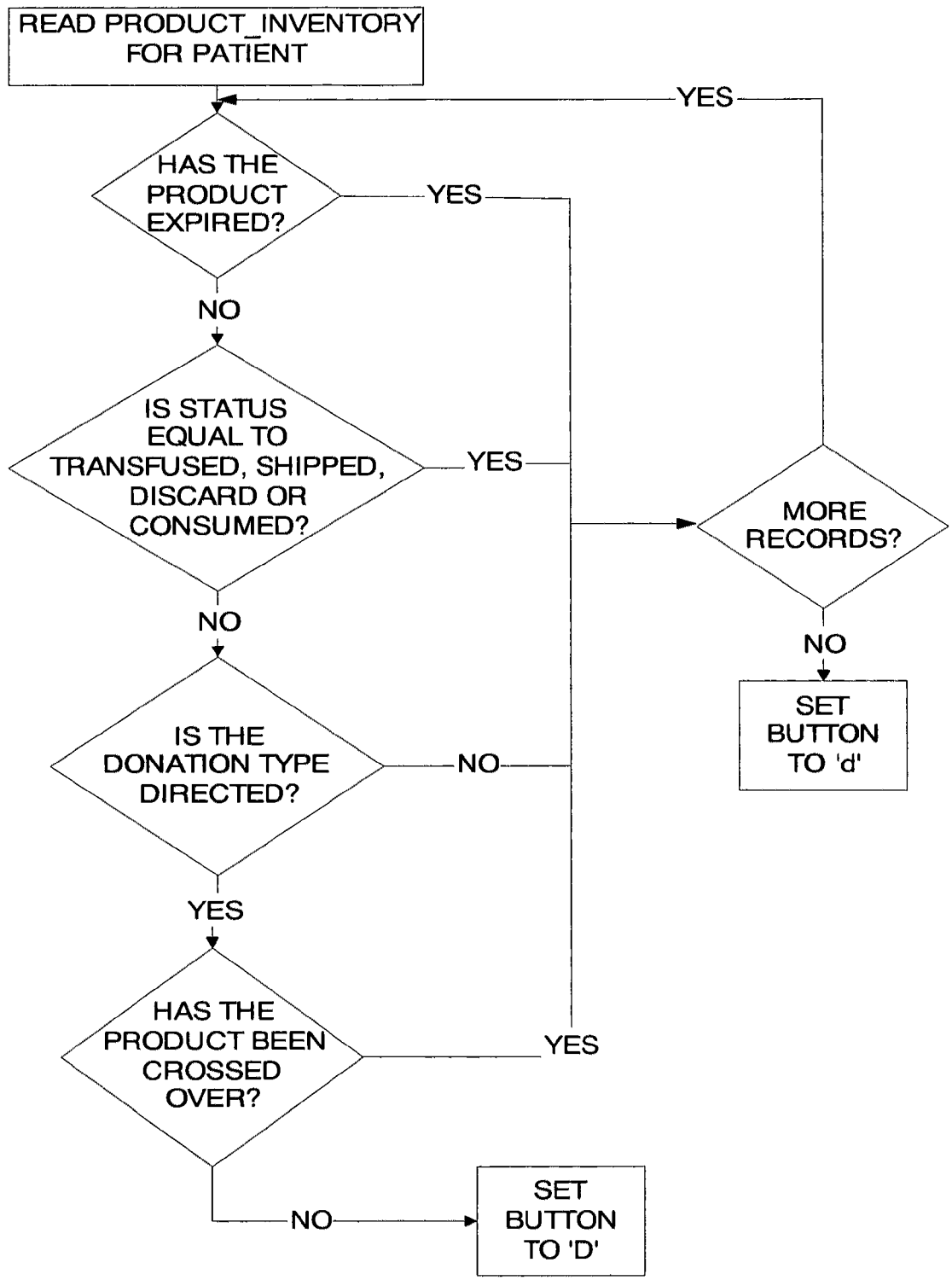
FIG. 13 is a flow chart of the logic used in button d of the patient bar.

The button d is a visual indication of a directed donation for the patient, not expired, not transfused, not shipped, not discarded, not consumed or crossed-over. If the button displays an uppercase "D", there is at least one such donation in inventory; otherwise, a lower case "d" means "none", as illustrated in FIG. 12.

Directed components are blood products (i.e. whole blood) which a donor has specifically designated for a particular patient's use. A patient who is scheduled for surgery where a transfusion may be required may have relatives or friends donate compatible blood specifically for use by a patient. This blood is categorized as directed and if deemed compatible is often preferred over other blood products available in the general inventory.

Significant antibodies indicate that the patient has had prior blood testing which has indicated the presence of unexpected or clinically significant antibodies, clinically significant antibodies being user-defined. The presence of these antibodies should be considered prior to issuing blood products for patient transfusion. The patient's blood attributes may constrain the blood products which are appropriate for use by the patient and/or require additional testing or modifications of blood products prior to transfusion.

Figure 14:
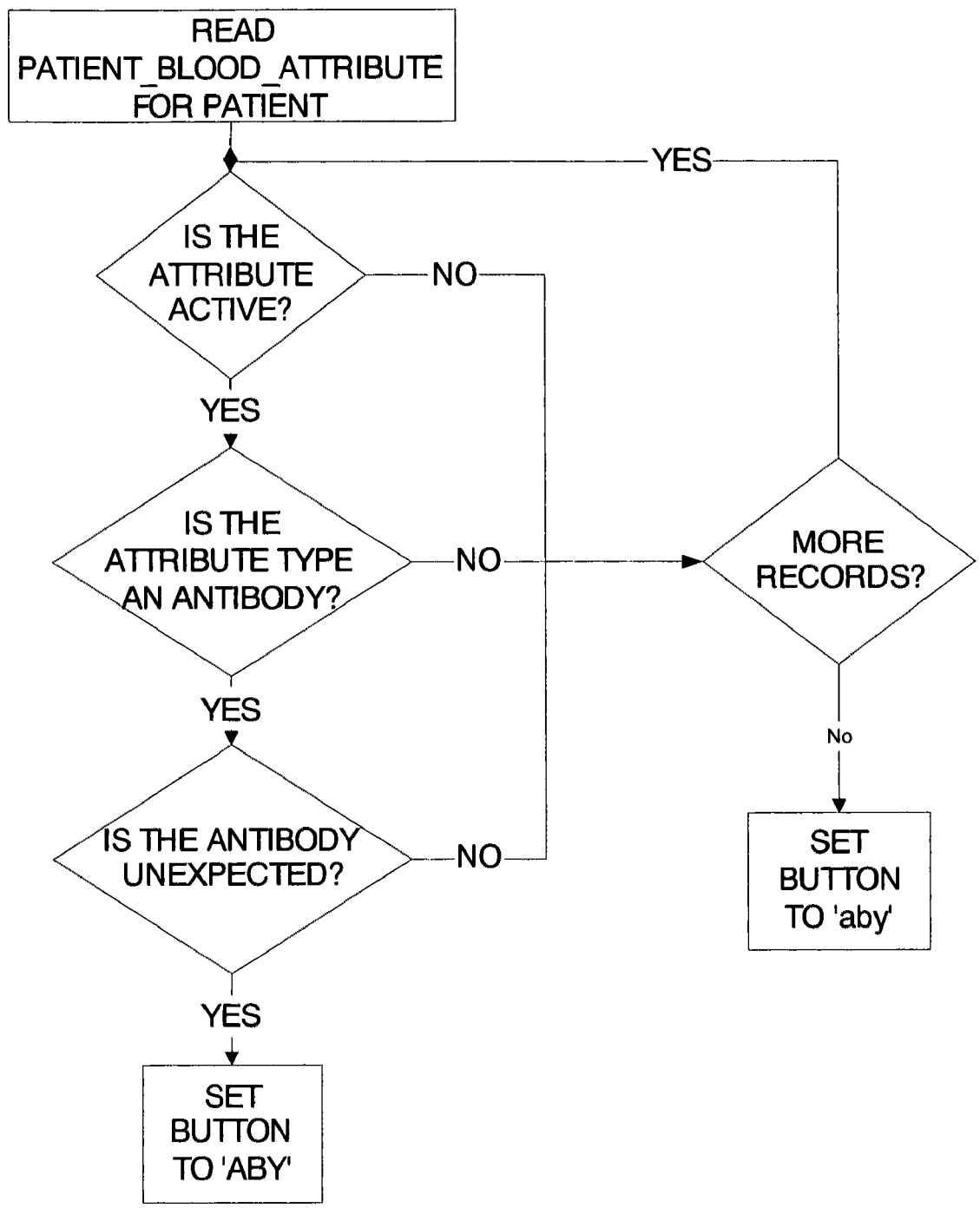
FIG. 14 is a flow chart of the logic used in button aby of the patient bar.

The button aby is an indication of whether the patient has unexpected antibody information. Referring to FIG. 14, if the button displays as upper case "ABY", there is information regarding unexpected antibodies; otherwise, lower case "aby" means "none" as illustrated in FIG. 14.

The next button presents the blood type of the patient, such as, "O Pos". This requires that the patient's blood type has been previously tested or was entered into the patient record. The blood type text contains the ABO and Rh components. The text for this is user modifiable but is generally standardized for ABO values, of "A, B, AB, O" and Rh values "POS" and "NEG". Therefore an example of a blood type caption presented might be "A POS". If the patient's blood type is unknown, the caption is left blank. Clicking on the blood type button accesses that information stored in the computer.

Figure 15:
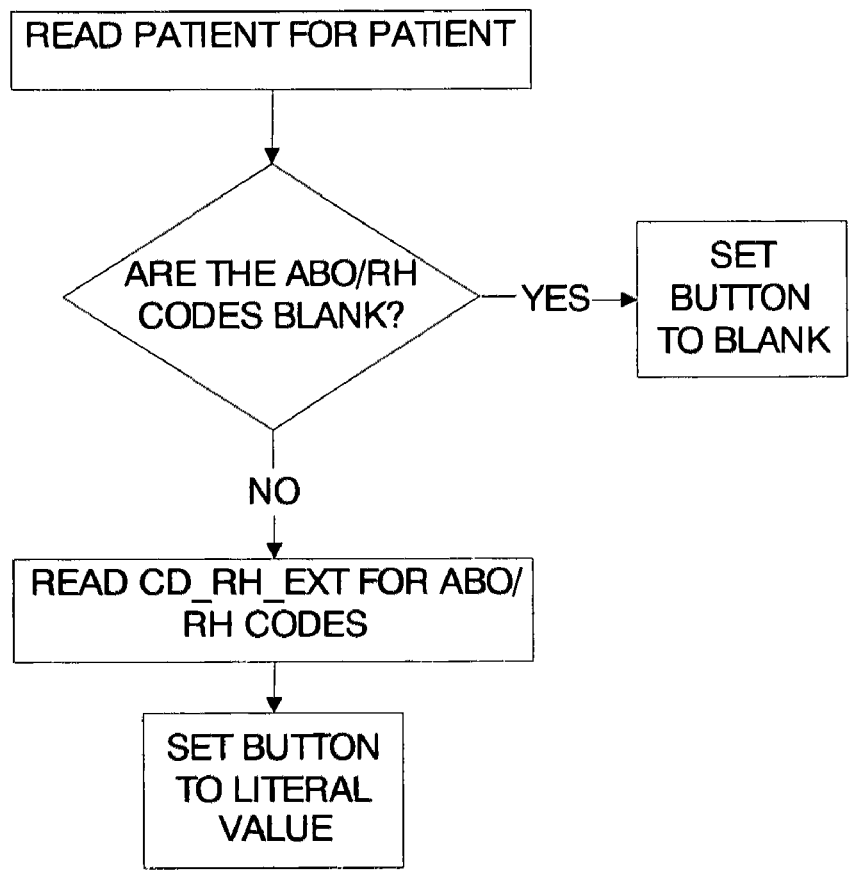
FIG. 15 is a flow chart of the logic used in conjunction with blood-type button "o-pos" of the patient bar.
Figure 16:
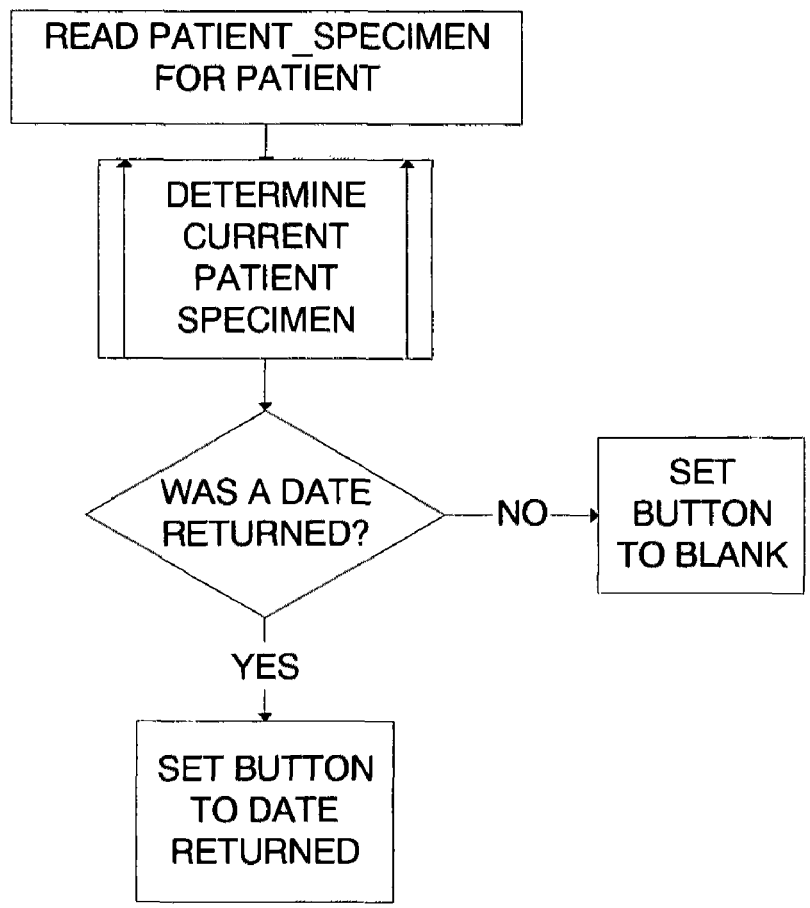
FIG. 16 is a flow chart of the logic used in conjunction with the specimen expiration date button of the patient bar.

The next button displays a patient's specimen expiration date. If there is a specimen that is current, active and available, then its expiration date displays as illustrated in FIG. 15. If no current active specimen is recorded for the patient or the specimen does not have an available status, no data is displayed on this button. Clicking on the button accesses the patient's specimen information stored in the computer.

Figure 17:
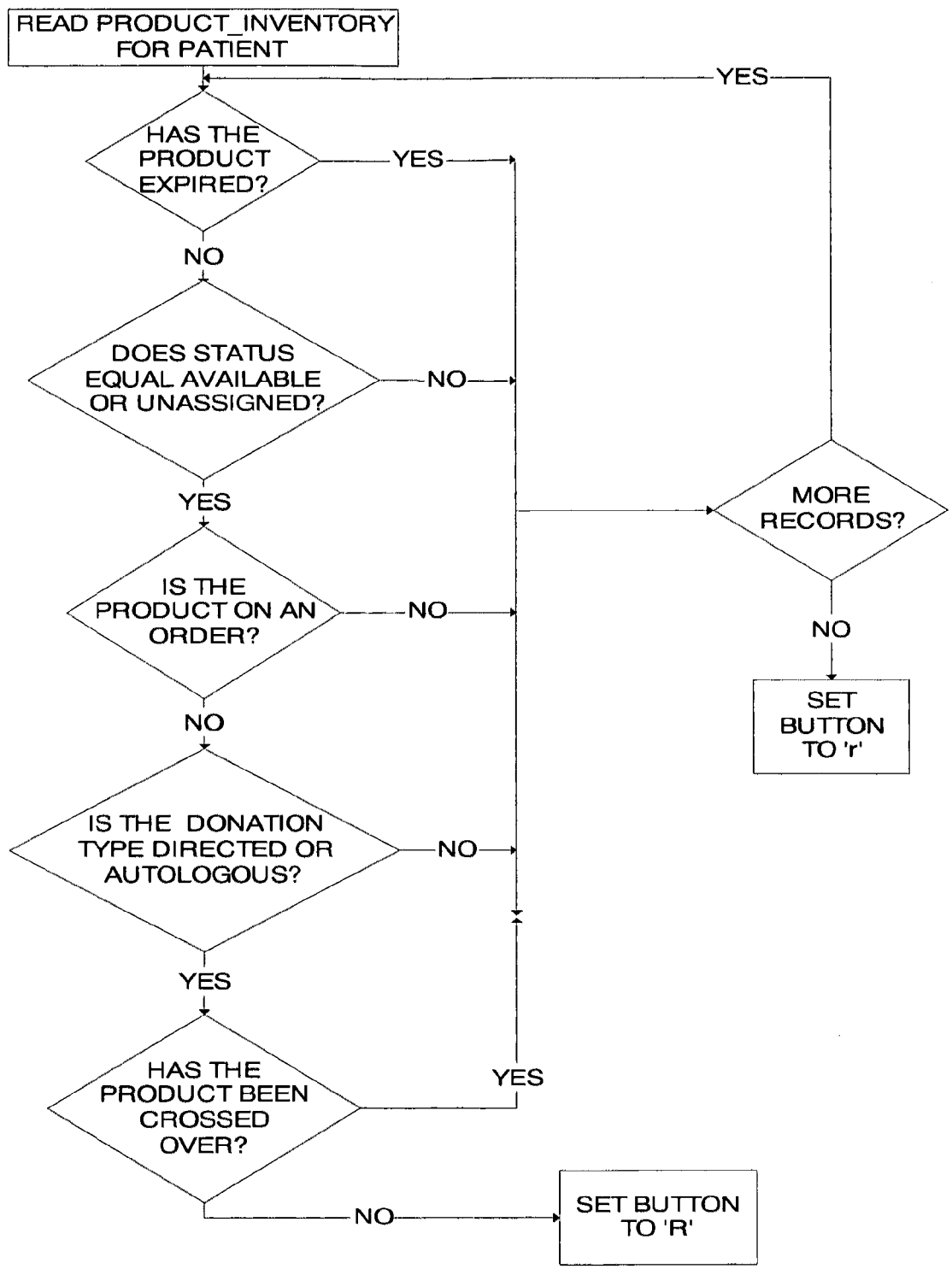
FIG. 17 is a flow chart of the logic used in conjunction with button r of the patient bar.

Reserved components are blood products which have been specifically linked for a particular patient's use. The button "r" indicates whether reserved components are available for the patient. If the button displays an uppercase "R", then there is at least one such component in inventory; otherwise, "r" means none, as illustrated in FIG. 17.

Patient information may be stored in the database and then accessed by finger-activated buttons for each category. For example, hematology test results for each patient may be entered or stored and accessed by a button, not shown, which will take the user directly to the patient's PATIENT HEMATOLOGY window on the screen. In the past, the RESERVE button was included on the bar P only when certain windows were accessed to provide information about whether any components are to be reserved for each patient. This can be a standard button, regardless of which window the user is on, and activation of the button will take the user directly to the RESERVED COMPONENTS FOR PATIENT window. Although not shown, an additional button may provide information about whether a component or derivative has been issued or transfused. Selecting the ISSUE button takes the user directly to the PATIENT TRANSFUSION INVESTIGATION form and performs an auto-query using the patient identification information.

As illustrated in the patient bar P of FIG. 8, each upper case letter will display if there is active information for a respective button; otherwise, a lower case letter is displayed. In addition, the bar P can be configured to display different colors for each button on the bar to bring attention to important information.

Figure 21:
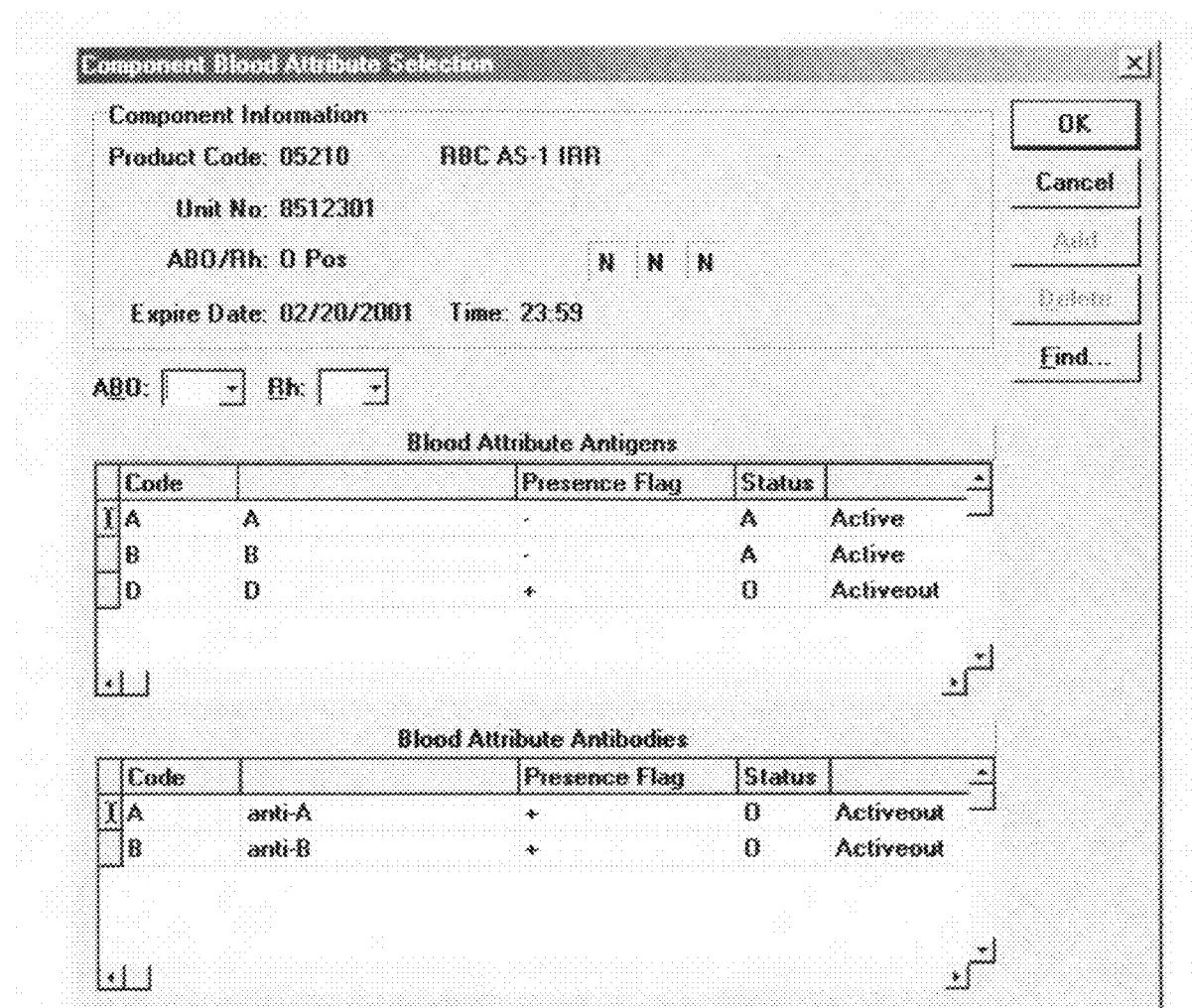
FIG. 21 is a screen display of component blood attribute information.
Figure 22:
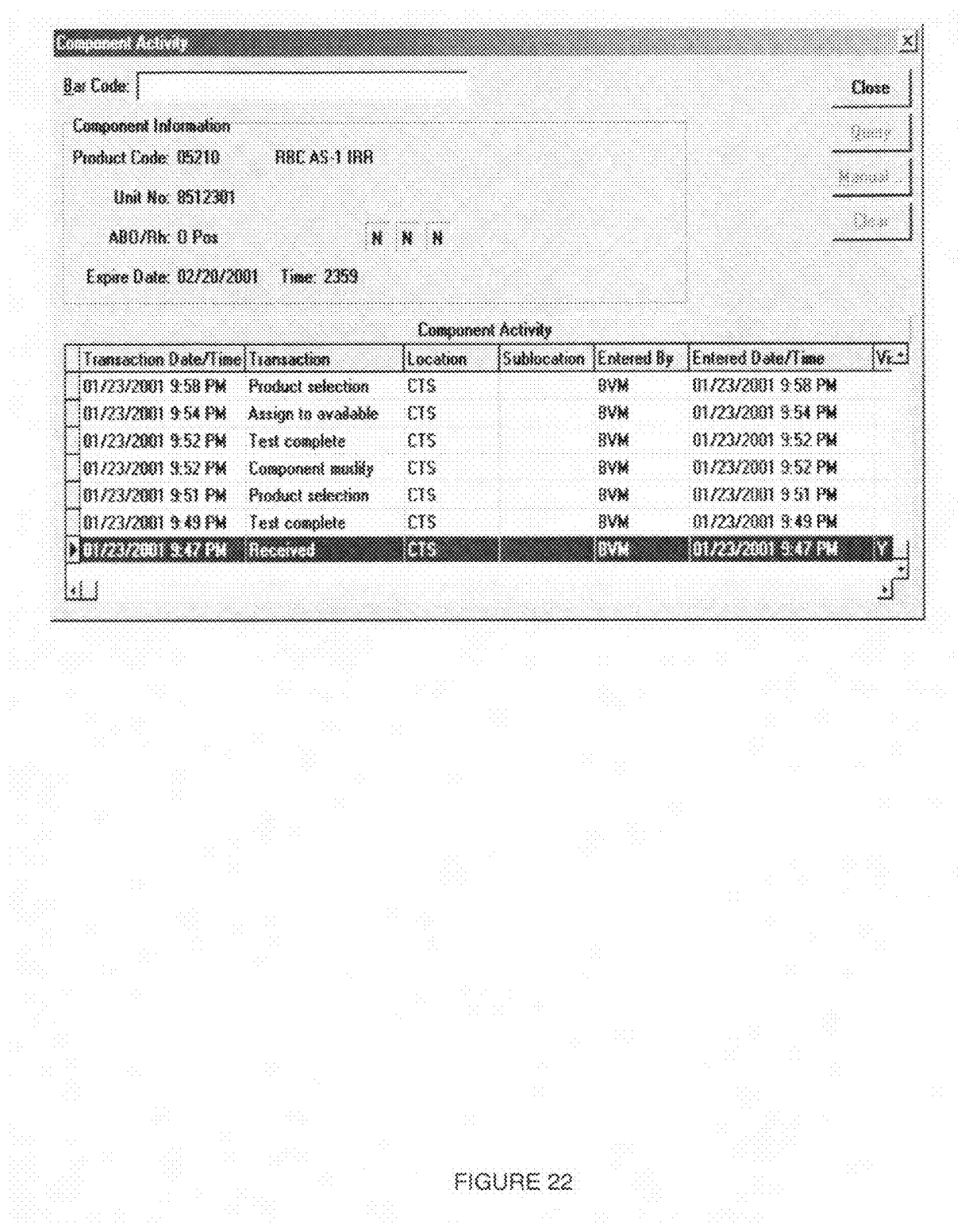

In practice, information relating to patient, blood products, component attributes may be recorded or stored in the database in the manner illustrated in FIGS. 20 to 22. As previously noted, FIG. 20 is a screen display of patient information including the patient bar P, FIG. 21 is a screen display of component blood attributes, and FIG. 22 illustrates information stored in tracking the location of blood components.

As soon as a blood component is received, it is assigned to a location within the central test facility. Throughout the life span of the blood component, the location of the component must be recorded, as illustrated in FIG. 22, before it can be transferred to another part of the facility or shipped outside the facility. If it is necessary to process the blood component, the computer verifies that the blood component is at the correct location for the work to be performed. Patient specimens and blood component segments are managed in a similar manner. Whenever a patient specimen or component segment is entered in the computer, it must be assigned to a location within the facility. The specimen or segment can only be used in processing if it resides at that location. If the specimen is needed by another facility, the transfer must be recorded in the computer system before it can be used by the receiving facility.

From the foregoing, FIGS. 1, 2 and 3 are intended to illustrate what is meant by "remote cross-matching" in which the cross-matching of each blood product and patient specimen is done at a facility remote from the patient. This avoids the necessity of maintaining a staff at each hospital but can only be done by maintaining records in the computer of the identity and location of the blood products and specimens.

FIG. 4 is intended more to show the logic for determining compatibility of a given blood product and specimen based on blood attributes as illustrated in FIGS. 5 and 6. Strictly speaking, this is not cross-matching but can be used as a preliminary step for cross-matching. Thus, the system is capable of verifying the updates of blood attributes of the patient as well as blood products to assure that they are compatible as more information becomes available. In conjunction with physical cross-matching, blood attribute determination is helpful in ascertaining the compatibility of a given blood product and specimen. FIG. 7 is intended more to show the alternative of emergency supply of blood where there is no time to cross-match or identify the patient and is intended more as a means of assuring that the blood made available can be used with virtually any patient.

While a number of exemplary aspects, embodiments and methods have been discussed above, those of skill in the art will recognize certain modifications, permutations, additions and subcombinations thereof. It is therefore intended that the following appended claims and claims hereafter introduced are interpreted to include all such modifications, permutations, additions and subcombinations as are within their true spirit and scope.

We claim:

1. A system for managing blood, blood components and blood derivatives wherein a computer is provided for processing data including a screen having a tool bar for displaying information, said system comprising:
    a database for entering information pertaining to a patient's blood, blood components and blood derivatives;
    said tool bar including means within said database for displaying each item of information related to each said patient;
    said means having a row or series of visual indicators for displaying the presence or absence of each said item of information; and
    said visual indicators including button icons buttons being driven by the current state of each said item in said database associated with each said button wherein activation of each said button corresponding to each said item present is operative to display said item on said screen.

2. The system according to claim 1 wherein said means comprises a first icon providing said patient's special needs information.

3. The system according to claim 1 wherein said means comprises a second icon for displaying said patient's transfusion reaction information.

4. The system according to claim 1 wherein said means comprises a third icon providing availability of blood component information.

5. The system according to claim 4 wherein said third icon includes displaying availability of directed blood component information.

6. The system according to claim 1 wherein said means comprises a fourth icon for displaying patient antibody and blood type information including but not limited to patient/product compatibility.

7. The system according to claim 1 wherein said means includes a fifth icon providing autologous blood component information.

8. The system according to claim 1 wherein said means includes a sixth icon providing information relating to expiration of a current patient specimen.

9. The system according to claim 8 wherein said sixth icon provides further information relating to expiration of reserved blood components.

10. A method for managing and tracking blood products in one or more hospitals in a single database provided for recording patient identification information and a method for displaying said information on a screen, comprising the steps of:
    storing each patient's special needs, prior transfusion reaction history, autologous blood availability and directed blood components in said database;
    providing a tool bar on said screen including a row or series of manually-activated buttons for identifying the presence or absence of each item of information stored; and
    activating each of said buttons to indicate the presence or absence of each said item of information stored;
    said buttons being driven by the current state of each said item in said database associated with each said button wherein activation of each said button corresponding to each said item present is operative to display said item on said screen.

11. The method according to claim 10, including the step of storing further items of information relating to blood type and patient specimen expiration date.

12. The method according to claim 10, whereupon activation of each said button automatically displays a symbol indicating the presence or absence of each said item of information stored.

13. The method according to claim 12, wherein said information displayed by each said button is represented by a capital letter and the absence of said information is represented by a lower case letter.

14. The method according to claim 10 including the step of recording special needs of each said patient on said database.

15. The method according to claim 10 including the step of carrying out patient/product compatibility by determining the patient blood attributes and the blood component attributes by their respective antigens and antibodies.

16. The method according to claim 10 including the step of recording prior transfusion reaction history of each said patient in said database.

17. The method according to claim 10 including the step of recording autologous blood availability in said database.

18. The method according to claim 10 including the step of recording blood type of each said blood product and said patient specimen.

19. The method according to claim 18 including the step of recording expiration dates of each said blood product and said patient specimen.

20. The method according to claim 10 including the step of recording on said database results of testing of each said patient specimen and said blood product.

21. The method according to claim 20 including the step of comparing blood attributes of each said patient specimen and said blood product.

22. The method according to claim 20 including the step of testing said blood product and said patient specimen at a blood-testing facility and tracking movement of each said blood product and said patient specimen between said facility and said hospitals.

23. The method according to claim 20 including the step of recording components of said blood products which have been reserved for said patient and indicating the presence of said reserved components in inventory.

24. A method for managing and tracking blood products in one or more hospital testing facilities, comprising the steps of:
   providing a processor having a single database configured for recording patient information;
   providing a display screen for displaying said information;
   storing each patient's special needs, prior transfusion reaction history, autologous blood availability and directed blood components in said database;
   providing a tool bar on said display screen including a plurality of manually-activated buttons in a row or series for identifying the presence or absence of each item of information stored;
   activating each of said buttons to display each said item of information stored in said database, said buttons being driven by the current state of each said item in said database associated with each said button wherein activation of each said button corresponding to each said item present is operative to display said item on said screen; and
   managing and tracking each of said blood products between said facilities.

25. A system for managing and locating patients' blood product information moveable between two or more blood testing facilities wherein a computer is provided for processing data including a screen for displaying information, said system comprising:
   a database in said computer for entering items of said blood product information including each patient's blood components and blood derivatives;
   a toolbar on said screen, and means within said database for selectively displaying said items on said screen related to each said patient;
   said toolbar having buttons provided with a row or series of visual indicators for displaying the presence or absence of each said item in said database; and
   wherein said buttons are driven by the current state of each of said items as well as the location in one of said facilities of each said blood product pertaining to each of said items displayed.

26. A system according to claim 25 wherein said buttons are interactive with one another in simultaneously displaying screens of selected said items pertaining to each patient.

27. A system according to claim 26 wherein the transfer of each of said blood components between said facilities is tracked in order for said blood components to be processed at the receiving one of said facilities.

* * * * *